US009593985B2

(12) United States Patent
Segal et al.

(10) Patent No.: US 9,593,985 B2
(45) Date of Patent: *Mar. 14, 2017

(54) TEMPERATURE MEASUREMENT SYSTEM AND METHOD

(71) Applicant: KINSA, INC., New York, NY (US)

(72) Inventors: Edo Segal, New York, NY (US); Kent Suzuki, Oakland, CA (US); Michael Fusaro, Smithfield, RI (US); Dmitro Panin, Zaporozhye (UA); Inder Singh, New York, NY (US)

(73) Assignee: KINSA, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/610,361

(22) Filed: Jan. 30, 2015

(65) Prior Publication Data

US 2015/0139277 A1    May 21, 2015

Related U.S. Application Data

(63) Continuation of application No. 13/871,660, filed on Apr. 26, 2013, now Pat. No. 8,974,115.

(Continued)

(51) Int. Cl.
*G01K 7/00* (2006.01)
*G01K 1/00* (2006.01)
(Continued)

(52) U.S. Cl.
CPC ............. *G01K 7/22* (2013.01); *A61B 5/01* (2013.01); *A61B 5/6898* (2013.01); *G01K 1/20* (2013.01);
(Continued)

(58) Field of Classification Search
USPC ............................... 374/141, 208, 163, 183
See application file for complete search history.

(56) References Cited

U.S. PATENT DOCUMENTS 3,241,370 A    3/1966    Mertler et al.
3,872,728 A    3/1975    Joyce et al.
(Continued)

FOREIGN PATENT DOCUMENTS

CN    2627780    7/2004
CN    102279060    12/2011
(Continued)

OTHER PUBLICATIONS

International Search Report and Written Opinion, dated Oct. 1, 2013, which issued during the prosecution of corresponding International Application No. PCT/US13/38609.

(Continued)

*Primary Examiner* — Mirellys Jagan
(74) *Attorney, Agent, or Firm* — Leason Ellis LLP

(57) ABSTRACT

In one or more implementations, a temperature measuring system is provided, including a temperature sensing probe having (a) a thermistor operatively connected to a first conductor and (b) a resistor operatively connected to a second conductor, and a temperature determination application stored in a memory of a computing device operatively connected to the temperature sensing probe. When executed by a processor of the computing device, the temperature determination application configures the computing device to: transmit a first instance of a signal to the first conductor, receive a temperature signal from the thermistor, the temperature signal corresponding to the first instance of the signal as output from the thermistor, transmit a second instance of the signal to the second conductor, receive a reference signal from the resistor, the reference signal corresponding to the second instance of the signal as output from the resistor, process the temperature signal and the reference signal to determine a relationship between the (Continued)

temperature signal and the reference signal, and compute a temperature based on the relationship.

15 Claims, 18 Drawing Sheets

Related U.S. Application Data

(60) Provisional application No. 61/639,399, filed on Apr. 27, 2012, provisional application No. 61/728,143, filed on Nov. 19, 2012, provisional application No. 61/732,066, filed on Nov. 30, 2012, provisional application No. 61/798,251, filed on Mar. 15, 2013.

(51) Int. Cl.
| | |
|---|---|
| G01K 7/22 | (2006.01) |
| G01K 1/20 | (2006.01) |
| A61B 5/00 | (2006.01) |
| A61B 5/01 | (2006.01) |
| G01K 13/00 | (2006.01) |
| G01K 15/00 | (2006.01) |
| H04M 1/02 | (2006.01) |

(52) U.S. Cl.
CPC ......... *G01K 13/002* (2013.01); *G01K 15/005* (2013.01); *H04M 1/0258* (2013.01); *A61B 5/0008* (2013.01); *A61B 2560/0223* (2013.01); *A61B 2562/227* (2013.01)

(56) References Cited

U.S. PATENT DOCUMENTS

| | | | |
|---|---|---|---|
| 3,906,796 | A | 9/1975 | Dumbeck |
| 4,031,365 | A | 6/1977 | Raggiotti et al. |
| 4,041,382 | A | 8/1977 | Washburn |
| 4,321,933 | A | 3/1982 | Baessler |
| 4,392,782 | A | 7/1983 | Kuehn, III et al. |
| 4,422,066 | A | 12/1983 | Belcourt et al. |
| 4,475,823 | A | 10/1984 | Stone |
| 5,050,430 | A | 9/1991 | Begin et al. |
| 6,234,964 | B1 | 5/2001 | Iliff |
| 6,440,069 | B1 | 8/2002 | Raymond et al. |
| 6,579,231 | B1 | 6/2003 | Phipps |
| 6,839,651 | B2 | 1/2005 | Lantz et al. |
| 6,925,324 | B2 | 8/2005 | Shusterman |
| 7,293,915 | B2 | 11/2007 | Chen |
| 7,870,249 | B2 | 1/2011 | Brown |
| 7,946,996 | B2 | 5/2011 | Callister et al. |
| 8,335,298 | B2 | 12/2012 | Clawson |
| 8,556,503 | B2 | 10/2013 | Tseng |
| 8,974,115 | B2 | 3/2015 | Segal et al. |
| 2001/0012913 | A1 | 8/2001 | Iliff |
| 2003/0002562 | A1 | 1/2003 | Yerlikaya et al. |
| 2003/0214999 | A1 | 11/2003 | Chapman et al. |
| 2004/0073459 | A1 | 4/2004 | Barthell |
| 2004/0103001 | A1 | 5/2004 | Mazar et al. |
| 2007/0185397 | A1 | 8/2007 | Govari et al. |
| 2008/0080593 | A1* | 4/2008 | Lane .................. G01K 13/002 374/208 |
| 2008/0103370 | A1 | 5/2008 | Dicks et al. |
| 2008/0177571 | A1 | 7/2008 | Rooney et al. |
| 2008/0200774 | A1 | 8/2008 | Luo |
| 2008/0221930 | A1 | 9/2008 | Wekell et al. |
| 2009/0124917 | A1* | 5/2009 | Hatlestad ............. A61B 5/0031 600/529 |
| 2009/0234916 | A1 | 9/2009 | Cosentino et al. |
| 2010/0039288 | A1 | 2/2010 | Mitchell et al. |
| 2010/0308980 | A1 | 12/2010 | Gosset et al. |
| 2010/0314443 | A1 | 12/2010 | Cudzilo |
| 2011/0064231 | A1 | 3/2011 | Goldberg et al. |
| 2011/0098966 | A1 | 4/2011 | Suzuki |
| 2011/0228810 | A1* | 9/2011 | O'Hara .................. G01J 5/0003 374/121 |
| 2011/0252003 | A1 | 10/2011 | Mitchell et al. |
| 2011/0270631 | A1 | 11/2011 | Cambray et al. |
| 2012/0099617 | A1 | 4/2012 | Tseng |
| 2012/0116184 | A1 | 5/2012 | Shieh |
| 2012/0220835 | A1 | 8/2012 | Chung |
| 2012/0226771 | A1 | 9/2012 | Harrington et al. |
| 2012/0244886 | A1 | 9/2012 | Blom et al. |
| 2012/0290266 | A1 | 11/2012 | Jain et al. |
| 2013/0179195 | A1 | 7/2013 | Lorsch |
| 2014/0086277 | A1 | 3/2014 | Sanchez et al. |
| 2014/0086278 | A1 | 3/2014 | Welland |
| 2014/0155708 | A1 | 6/2014 | Petersen et al. |
| 2014/0216136 | A1 | 8/2014 | Yim |
| 2014/0243637 | A1 | 8/2014 | Rahman et al. |

FOREIGN PATENT DOCUMENTS

| | | |
|---|---|---|
| EP | 2098863 | 9/2009 |
| EP | 2 849 633 | 3/2015 |
| GB | 2 256 051 | 11/1992 |
| WO | WO 86/00539 | 1/1986 |
| WO | WO 2013066642 | 5/2013 |
| WO | WO 2013134845 | 9/2013 |
| WO | WO 2013/170378 | 11/2013 |

OTHER PUBLICATIONS

International Preliminary Report on Patentability, dated May 27, 2014, which issued during the prosecution of corresponding International Application No. PCT/US13/38609.
International Preliminary Report on Patentability, dated Jul. 29, 2014, which issued during the prosecution of corresponding International Application No. PCT/US13/38609.
Non-Final Office Action in corresponding U.S. Appl. No. 13/871,660, mailed Jul. 28, 2014.
Final Office Action in corresponding U.S. Appl. No. 13/871,660, mailed Dec. 30, 2014.
Ginsberg J, Mohebbi MH, Patel RS, Brammer L, Smolinski MS, Brilliant L.; "Detecting Influenza Epidemics Using Search Engine Query Date," Nature Feb. 19, 2009; vol. 457:1012-4.
"Examples of Mobile Apps for Which the FDA Will Exercise Enforcement Discretion." U.S. Food and Drug Administration. N.p., Jun. 11, 2014. Web. <http://www.fda.gov/MedicalDevices/ProductsandMedicalProcedures/ConnectedHealth/MobileMedicalApplications/ucm368744.htm>.
Boulos, Maged N Kamel, Steve Wheeler, Carlos Tavares, and Ray Jones. "How Smartphones Are Changing the Face of Mobile and Participatory Healthcare: An Overview, with Example from ECAALYX." BioMedical Engineering OnLine. BioMed Central, 2011. Web. <http://www.ncbi.nlm.nih.gov/pmc/articles/PMC3080339/>.
Istepanian, R.S.H. et al. "Guest Editorial Introduction to the Special Section on M-Health: Beyond Seamless Mobility and Global Wireless Health-Care Connectivity" IEEE Transactions on Information Technology in Biomedicine, vol. 8, No. 4, Dec. 2004. pp. 405-414.
K. Dinesh kumar. "Human Health Monitoring Mobile Phone Application by Using the Wireless Nanosensor Based Embedded System" International Conference on Information Communication and Embedded Systems (ICICES 2013), 889-92, Feb. 21-22, 2013.

* cited by examiner

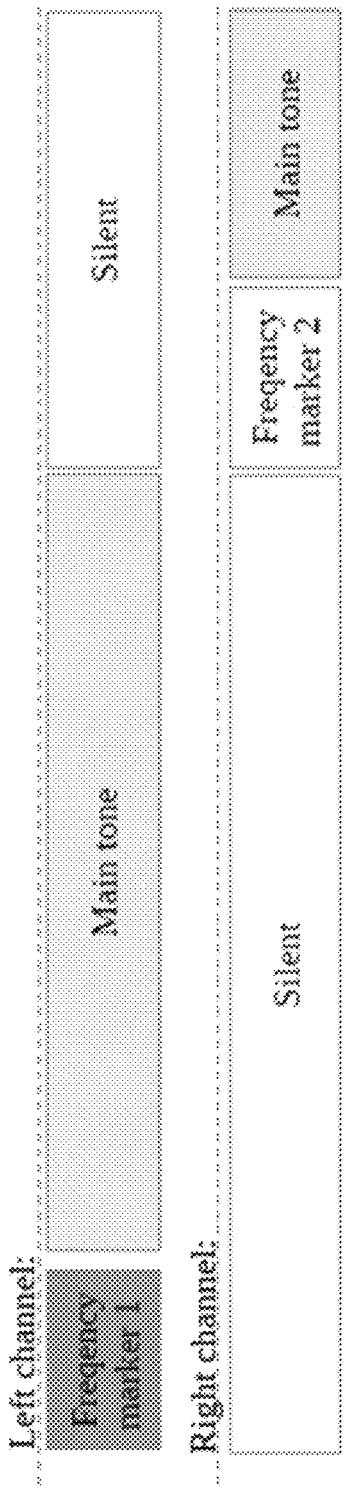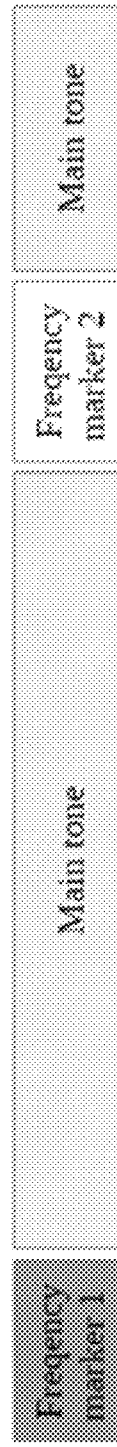
FIG. 13

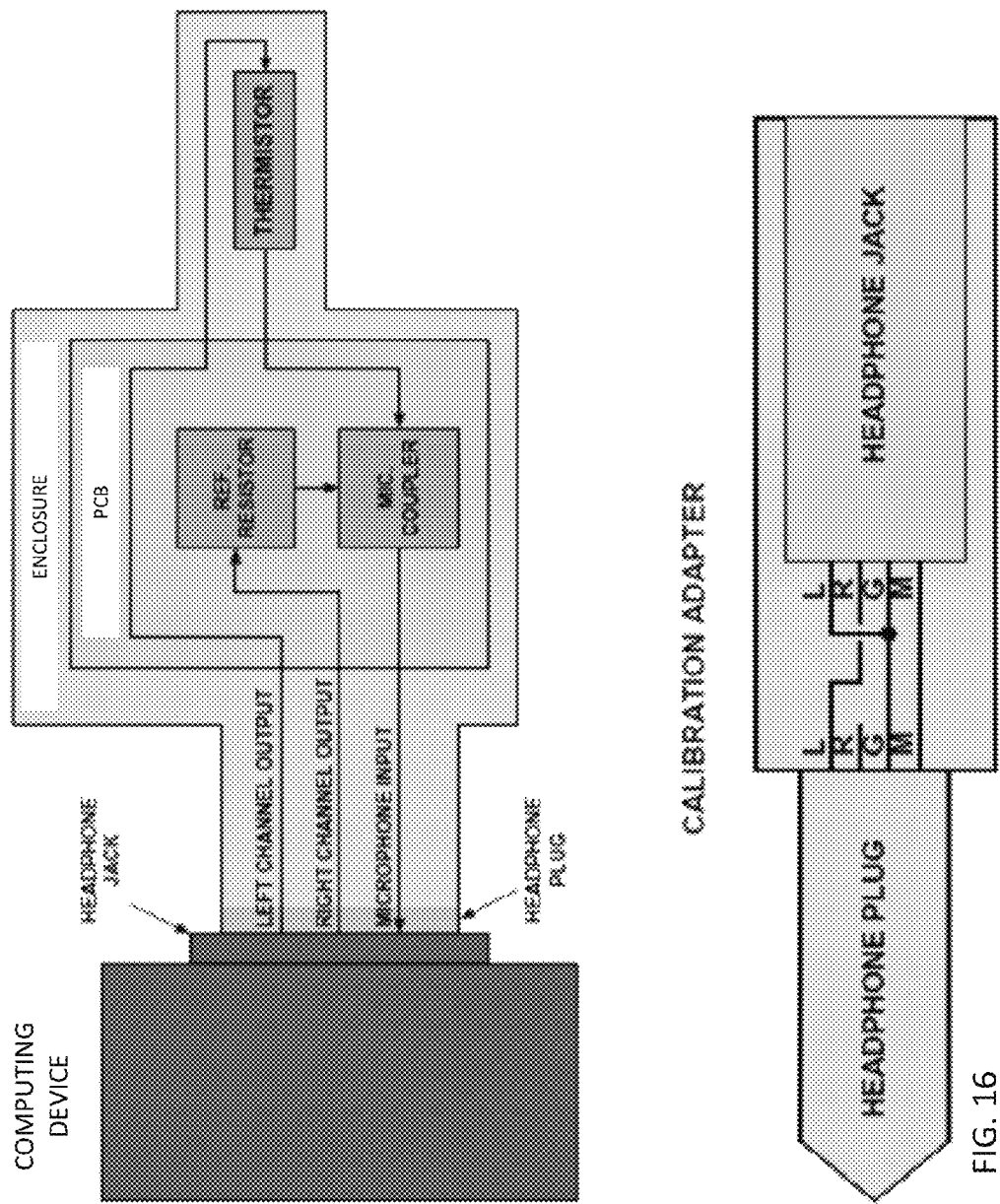

TEMPERATURE MEASUREMENT SYSTEM AND METHOD

CROSS-REFERENCE TO RELATED APPLICATIONS

This application is a continuation of U.S. application Ser. No. 13/871,660, filed Apr. 26, 2013, which claims the benefit of priority under 35 U.S.C. Section 119(e) of U.S. Application Ser. No. 61/639,399, filed on Apr. 27, 2012, U.S. Application Ser. No. 61/728,143, filed on Nov. 19, 2012, U.S. Application Ser. No. 61/732,066, filed on Nov. 30, 2012, and U.S. Application Ser. No. 61/798,251, filed on Mar. 15, 2013, the contents of each of which is hereby incorporated by reference in its respective entirety.

TECHNICAL FIELD OF THE INVENTION

This patent application relates generally to the field of temperature measurement.

BACKGROUND OF THE INVENTION

A person's body temperature is one of four "vital signs" to measure and determine a person's health state. "Normal" body temperature may range from 97.8 degrees F. (e.g., 36.5 degrees C.) to 99 degrees F. (37.2 degrees C.) for a healthy adult. Deviations from this range, even in small increments, may represent a significant health issue.

Over time, thermometers have been developed to take a person's body temperature, often orally (e.g., by mouth). Temperature may also be taken rectally, axillary (under the arm), by ear or other area, e.g., forehead. Classic glass thermometers have been recently replaced by digital thermometers. Despite advancements in thermometers to measure a person's body temperature, significant limitations still exist.

With the continued proliferation of mobile computing devices (e.g., smartphones, PDAs, etc.), many individuals have become increasingly reliant on such devices in order to perform routine activities. For example, many mobile device users perform multiple communication tasks (phone calls, emails, text messaging, etc.), shopping tasks (price comparisons, ecommerce transactions, etc.) and entertainment tasks (media watching/listening) with their mobile devices.

Various peripherals/accessories exist that connect to/interface with mobile devices in order to provide such devices with additional functionality. However, such accessories are often fairly expensive, owing to (a) the considerable engineering efforts required in order to develop them, (b) the considerable cost of their materials/manufacture, and (c) licensing fees that certain mobile device manufacturers demand in order to certify such peripherals as being compatible with a particular mobile device.

It is with respect to these and other considerations that the disclosure made herein is presented.

SUMMARY OF THE INVENTION

In accordance with one or more implementations of the invention, a temperature measuring system and method are provided that comprise a temperature sensing probe comprising a thermistor operatively connected to a first conductor, a resistor operatively connected to a second conductor, and a computing device operatively connected to the temperature sensing probe. The computing device may be configured to transmit a first instance of a signal to the first conductor and to receive a temperature signal from the thermistor, the temperature signal comprising the first instance of the signal as output from the thermistor. The computing device may be further configured to transmit a second instance of the signal to the second conductor, and to receive a reference signal from the resistor, the reference signal comprising the second instance of the signal as output from the resistor. The computing device may be further configured to process the temperature signal and the reference signal to determine a relationship between the temperature signal and the reference signal, and to compute a temperature based on the relationship.

In accordance with one or more implementations of the invention, the temperature sensing probe further comprises a switch, the switch being configured to (a) disconnect the first conductor and the thermistor, and (b) operatively connect the first conductor and the resistor upon activation of the switch. The computing device may be further configured to transmit a third instance of the signal to the first conductor and to receive a calibration signal from the resistor, the calibration signal comprising the third instance of the signal as output from the resistor. The computing device may be further configured to process the calibration signal with the reference signal to identify a discrepancy between the calibration signal and the reference signal, and calibrate one or more subsequent temperature computations based on the discrepancy.

In accordance with one or more implementations of the invention, the temperature measuring system and method may further comprise a calibration adapter that is configured to (a) disconnect the first conductor and the thermistor, and (b) operatively connect the first conductor and the resistor. The computing device may be further configured to transmit a third instance of the signal to the first conductor and to receive a calibration signal from the resistor, the calibration signal comprising the third instance of the signal as output from the resistor. The computing device may be further configured to process the calibration signal with the reference signal to identify a discrepancy between the calibration signal and the reference signal, and to calibrate one or more subsequent temperature computations based on the discrepancy.

In accordance with one or more implementations of the invention, a temperature measuring system and method are provided that comprise a temperature sensing probe comprising a thermistor, a resistor, a power source, an amplifier, a signal selector that is operable to connect voltage from the thermistor or the resistor to the amplifier, and a voltage controlled oscillator configured to receive an amplified signal from the amplifier and to generate a reference signal or a temperature signal. Moreover, a computing device is included that is operatively connected to the temperature sensing probe and that may be configured to selectively transmit a control signal to control the signal selector and to receive the reference signal from the voltage controlled oscillator, the reference signal comprising output from the voltage controlled oscillator when the voltage controlled oscillator is configured to receive output from the resistor. The computing device may be further configured to receive the temperature signal from the voltage controlled oscillator, the temperature signal comprising output from the voltage controlled oscillator when the voltage controlled oscillator is configured to receive output from the thermistor. The computing device may be further configured to process the reference signal and the temperature signal to determine a relationship between the temperature signal and the reference signal, to compute a temperature based on the relationship and to display the temperature.

In accordance with one or more implementations of the invention, a temperature measuring system and method are provided that comprise a computing device that is operatively coupled to a temperature sensing probe. The temperature sensing probe comprises a thermistor, a resistor, a processor, a power source that provides voltage to at least the thermistor and the resistor, a signal selector that is operable to connect voltage from the thermistor or the resistor to the processor, and a signal conditioner that is operable to output a signal to the computing device. The processor may be configured to alternately read a reference signal that comprises output associated with the resistor, and read a temperature signal that comprises output associated with the thermistor. The processor may be further configured to calculate a temperature value as a function of the reference signal and the temperature signal, and to transmit the temperature value to the computing device via the signal conditioner, wherein the computing device displays a temperature associated with the temperature value.

These and other aspects, features, and advantages can be appreciated from the accompanying description of certain embodiments of the invention and the accompanying drawing figures and claims.

BRIEF DESCRIPTION OF THE DRAWINGS

FIG. 13 illustrates an example output stereo stream and a corresponding input monaural ("mono") stream.

FIG. 16 is a circuit diagram illustrating an example calibration adapter in accordance with the present application.

DETAILED DESCRIPTION OF CERTAIN EMBODIMENTS OF THE INVENTION

By way of overview and introduction, various systems, methods, and apparatuses are described herein that facilitate and enable temperature measurement. A temperature sensing probe having a thermistor and a resistor is configured for input into the headphone jack of a computing device, such as a smartphone (e.g., devices running the iOS, DROID, WINDOWS Phone, and BLACKBERRY operating systems). Signals, such as audio tones, can be transmitted by the computing device through the headphone jack to conductors of the temperature sensing probe, such as a connector that is coupled to the thermistor. In one or more implementations, various signals are returned from the temperature sensing probe and can be used to compute a temperature that is sensed at the probe. In certain implementations, the probe can be configured as an oral thermometer, thought it should be understood that the systems, methods, and apparatuses described herein can be similarly configured as other types of thermometers, as can be appreciated by those of ordinary skill in the art.

The following detailed description is directed to systems, methods, and apparatuses for temperature measurement. The referenced systems, methods, and apparatuses are now described more fully with reference to the accompanying drawings, in which one or more illustrated embodiments and/or implementations of the systems, methods, and apparatuses are shown. The systems, methods, and apparatuses are not limited in any way to the illustrated embodiments and/or implementations as the illustrated embodiments and/or implementations described below are merely exemplary of the systems, methods, and apparatuses, which can be embodied in various forms, as appreciated by one skilled in the art. Therefore, it is to be understood that any structural and functional details disclosed herein are not to be interpreted as limiting the systems, methods, and apparatuses, but rather are provided as a representative embodiment and/or implementation for teaching one skilled in the art one or more ways to implement the systems, methods, and apparatuses. Accordingly, aspects of the present systems, methods, and apparatuses can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Furthermore, the terms and phrases used herein are not intended to be limiting, but rather are to provide an understandable description of the systems and methods.

Figure 1A:
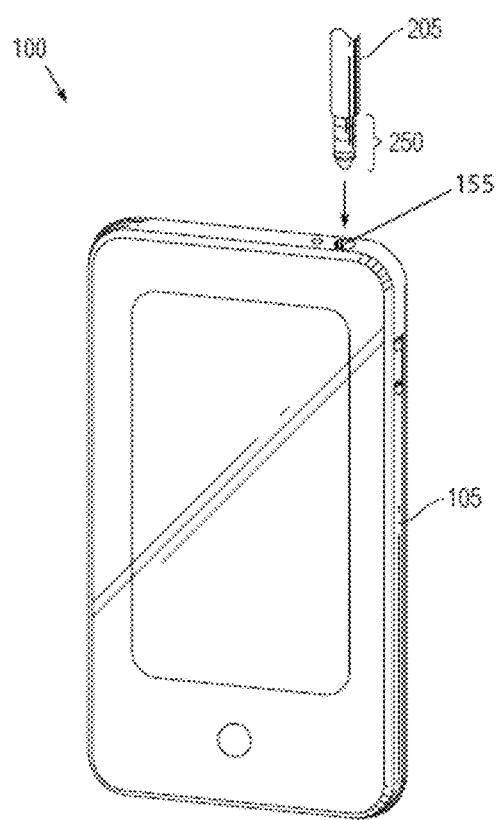
FIG. 1A is a high-level diagram illustrating an exemplary configuration of a temperature measuring system in accordance with at least one embodiment disclosed herein.

An exemplary temperature measuring system 100 is shown in FIG. 1A. In one implementation, temperature measuring system 100 includes a computing device 105, such as a smartphone or PDA. Computing device 105 will be illustrated and described in greater detail with respect to FIG. 1B. Temperature measuring system 100 may further include a temperature sensing probe 205. Temperature sensing probe 205 will be illustrated and described in greater detail with respect to FIG. 2. It should be understood, as illustrated in FIG. 1A, that temperature sensing probe 205 includes a projecting connector/plug 250, such as a TRS or TRRS connector, as are known to those of ordinary skill in the art. Temperature sensing probe 205 may be constructed such that the connector 250 can be inserted into an input/output cavity 155 of computing device 105, such as a headphone jack (TRS/TRRS input), as shown in FIG. 1A and as is known to those of ordinary skill in the art. A further illustration of input cavity 155 is shown in FIG. 1C.

Figure 1B:
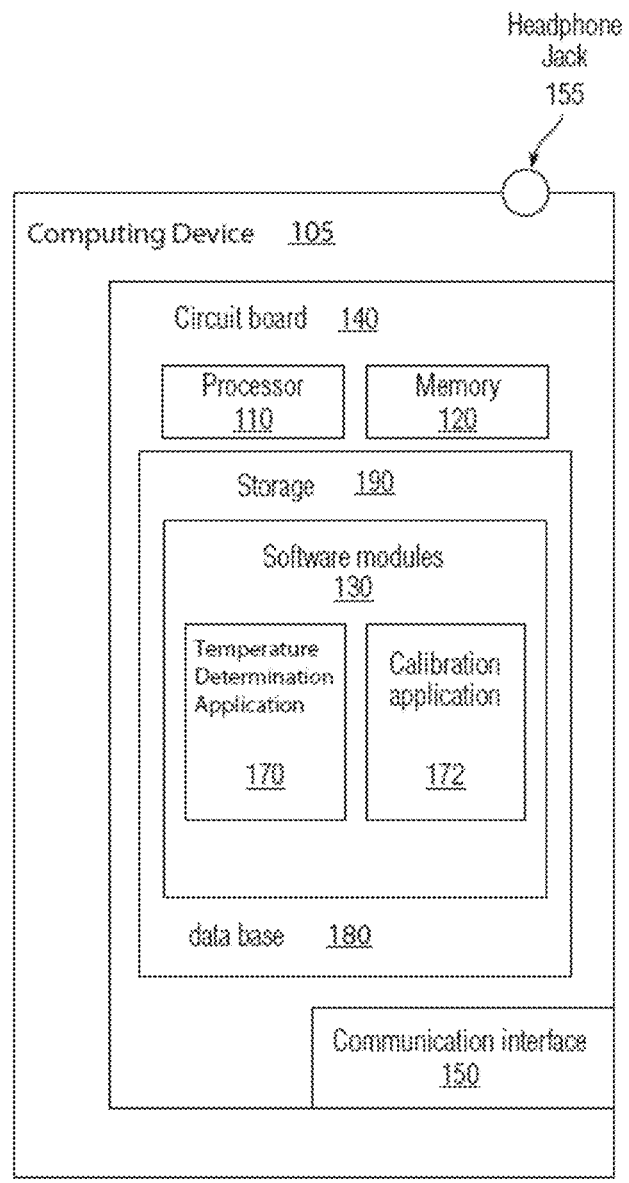
FIG. 1B is a high-level diagram illustrating an exemplary configuration of a computing device in accordance with at least one embodiment disclosed herein.
Figure 1C:
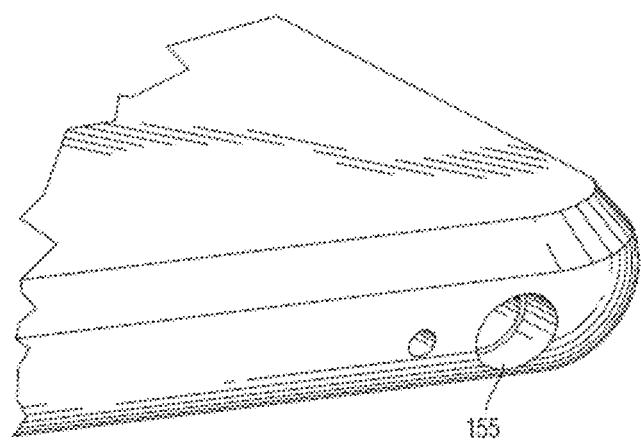
FIG. 1C is an illustration of an input cavity/jack of a computing device in accordance with at least one embodiment disclosed herein.

Turning now to FIG. 1B, a high-level diagram illustrating an exemplary configuration of computing device 105 is shown. In one implementation, computing device 105 can be a personal computer or server. In other implementations, computing device 105 can be a tablet computer, a laptop computer, or a mobile device/smartphone, though it should be understood that computing device 105 can be practically any computing device and/or data processing apparatus capable of embodying the systems and/or methods described herein.

Computing device 105 includes a circuit board 140, such as a motherboard, which is operatively connected to various hardware and software components that serve to enable operation of the temperature measuring system 100. The circuit board 140 is operatively connected to a processor 110 and a memory 120. Processor 110 serves to execute instructions for software that can be loaded into memory 120. Processor 110 can be a number of processors, a multi-processor core, or some other type of processor, depending on the particular implementation. Further, processor 110 can be implemented using a number of heterogeneous processor systems in which a main processor is present with secondary processors on a single chip. As another illustrative example, processor 110 can be a symmetric multi-processor system containing multiple processors of the same type.

In one or more implementations, memory 120 and/or storage 190 are accessible by processor 110, thereby enabling processor 110 to receive and execute instructions stored on memory 120 and/or on storage 190. Memory 120 can be, for example, a random access memory (RAM) or any other suitable volatile or non-volatile computer readable storage medium. In addition, memory 120 can be fixed or removable. Storage 190 can take various forms, depending on the particular implementation. For example, storage 190 can contain one or more components or devices such as a hard drive, a flash memory, a rewritable optical disk, a rewritable magnetic tape, or some combination of the above. Storage 190 also can be fixed or removable.

One or more software modules 130 are encoded in storage 190 and/or in memory 120. The software modules 130 can comprise one or more software programs or applications having computer program code or a set of instructions executed in processor 110. Such computer program code or instructions for carrying out operations for aspects of the systems and methods disclosed herein can be written in any combination of one or more programming languages, including an object oriented programming language such as Java, Smalltalk, C++, Python, and JavaScript or the like and conventional procedural programming languages, such as the "C" programming language or similar programming languages. The program code can execute entirely on computing device 105, partly on computing device 105, as a stand-alone software package, partly on computing device 105 and partly on a remote computer/device, or entirely on the remote computer/device or server. In the latter scenario, the remote computer can be connected to computing device 105 through any type of network, including a local area network (LAN) or a wide area network (WAN), or the connection can be made to an external computer (for example, through the Internet using an Internet Service Provider).

One or more software modules 130, including program code/instructions, are located in a functional form on one or more computer readable storage devices (such as memory 120 and/or storage 190) that can be selectively removable. The software modules 130 can be loaded onto or transferred to computing device 105 for execution by processor 110. It can also be said that the program code of software modules 130 and one or more computer readable storage devices (such as memory 120 and/or storage 190) form a computer program product that can be manufactured and/or distributed in accordance with the present invention, as is known to those of ordinary skill in the art.

It should be understood that in some illustrative embodiments, one or more of software modules 130 can be downloaded over a network to storage 190 from another device or system via communication interface 150 for use within temperature measuring system 100. For instance, program code stored in a computer readable storage device in a server can be downloaded over a network from the server to temperature measuring system 100.

Included among the software modules 130 may be temperature determination application 170 and/or a calibration application 172, each of which can be executed by processor 110. During execution of the software modules 130, and specifically the temperature determination application 170 and/or the calibration application 172, the processor 110 configures the circuit board 140 to perform various operations relating to temperature determination/calibration with computing device 105, as will be described in greater detail below. It should be understood that while software modules 130, temperature determination application 170 and/or calibration application 172 can be embodied in any number of computer executable formats, in certain implementations software modules 130, temperature determination application 170 and/or calibration application 172 comprise one or more applications that are configured to be executed at computing device 105 in conjunction with one or more applications or 'apps' executing at remote devices, and/or one or more viewers such as internet browsers and/or proprietary applications. Furthermore, in certain implementations, software modules 130, temperature determination application 170 and/or calibration application 172 can be configured to execute at the request or selection of a user of another computing device (or any other such user having the ability to execute a program in relation to computing device 105, such as a network administrator), while in other implementations computing device 105 can be configured to automatically execute software modules 130, temperature determination application 170 and/or calibration application 172, without requiring an affirmative request to execute. It should also be noted that while FIG. 1B depicts memory 120 oriented on circuit board 140, in an alternate implementation, memory 120 can be operatively connected to the circuit board 140. In addition, it should be noted that other information and/or data relevant to the operation of the present systems and methods (such as database 180) can also be stored on storage 190, as will be discussed in greater detail below.

Also stored on storage 190 may be database 180. In certain implementations, database 180 contains and/or maintains various data items and elements that are utilized throughout the various operations of temperature measuring system 100, in a manner known to those of ordinary skill in the art. It should be noted that although database 180 is depicted as being configured locally to computing device 105, in certain implementations database 180 and/or various of the data elements stored therein can be located remotely (such as on a remote device or server—not shown) and connected to computing device 105 through a network, in a manner known to those of ordinary skill in the art.

Communication interface 150 is also operatively connected to circuit board 140. Communication interface 150 can be any interface that enables communication between the computing device 105 and external devices, machines and/or elements. Communication interface 150 may include, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting computing device 105 to other computing devices and/or communication networks such as private networks and the Internet. Such connections can include a wired connection or a wireless connection (e.g., using the 802.11 standard) though it should be understood that communication interface 150 can be practically any interface that enables communication to/from the circuit board 140.

At various points during the operation of temperature measuring system 100, computing device 105 can communicate with one or more computing devices, such as those controlled and/or maintained by one or more individuals and/or entities. Such computing devices may transmit and/or receive data to/from computing device 105, thereby initiating maintaining, and/or enhancing the operation of the temperature measuring system 100, in a manner known to those of ordinary skill in the art. It should be understood that such computing devices can be in direct communication with computing device 105, indirect communication with computing device 105, and/or can be communicatively coordinated with computing device 105, as is known to those of ordinary skill in the art.

In the description that follows, certain embodiments and/or implementations are described with reference to acts and symbolic representations of operations that are performed by one or more devices, such as the temperature measuring system 100 of FIG. 1A. As such, it will be understood that such acts and operations, which are at times referred to as being computer-executed or computer-implemented, include the manipulation by processor 110 of electrical signals representing data in a structured form. This manipulation transforms the data and/or maintains them at locations in the memory system of the computer (such as memory 120 and/or storage 190), which reconfigures and/or otherwise alters the operation of the system in a manner understood by those skilled in the art. The data structures in which data are maintained are physical locations of the memory that have particular properties defined by the format of the data. However, while an embodiment is being described in the foregoing context, it is not meant to provide architectural limitations to the manner in which different embodiments can be implemented. The different illustrative embodiments can be implemented in a system including components in addition to or in place of those illustrated for the temperature measuring system 100. Other components shown in FIGS. 1A and 1B can be varied from the illustrative examples shown. The different embodiments can be implemented using any hardware device or system capable of running program code. In another illustrative example, temperature measuring system 100 can take the form of a hardware unit that has circuits that are manufactured or configured for a particular use. This type of hardware can perform operations without needing program code to be loaded into a memory from a computer readable storage device to be configured to perform the operations.

For example, computing device 105 can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules 130 can be omitted because the processes for the different embodiments are implemented in a hardware unit.

In still another illustrative example, computing device 105 can be implemented using a combination of processors found in computers and hardware units. Processor 110 can have a number of hardware units and a number of processors that are configured to execute software modules 130. In this example, some of the processors can be implemented in the number of hardware units, while other processors can be implemented in the number of processors.

In another example, a bus system can be implemented and can be comprised of one or more buses, such as a system bus or an input/output bus. Of course, the bus system can be implemented using any suitable type of architecture that provides for a transfer of data between different components or devices attached to the bus system. Additionally, communications interface 150 can include one or more devices used to transmit and receive data, such as a modem or a network adapter.

Embodiments and/or implementations can be described in a general context of computer-executable instructions, such as program modules, being executed by a computer. Generally, program modules include routines, programs, objects, components, data structures, etc., that perform particular tasks or implement particular abstract data types.

It should be further understood that while the various computing devices and machines referenced herein, including but not limited to computing device 105, are referred to herein as individual/single devices and/or machines, in certain implementations the referenced devices and machines, and their associated and/or accompanying operations, features, and/or functionalities can be arranged or otherwise employed across any number of devices and/or machines, such as over a network connection, as is known to those of skill in the art.

Figure 2:
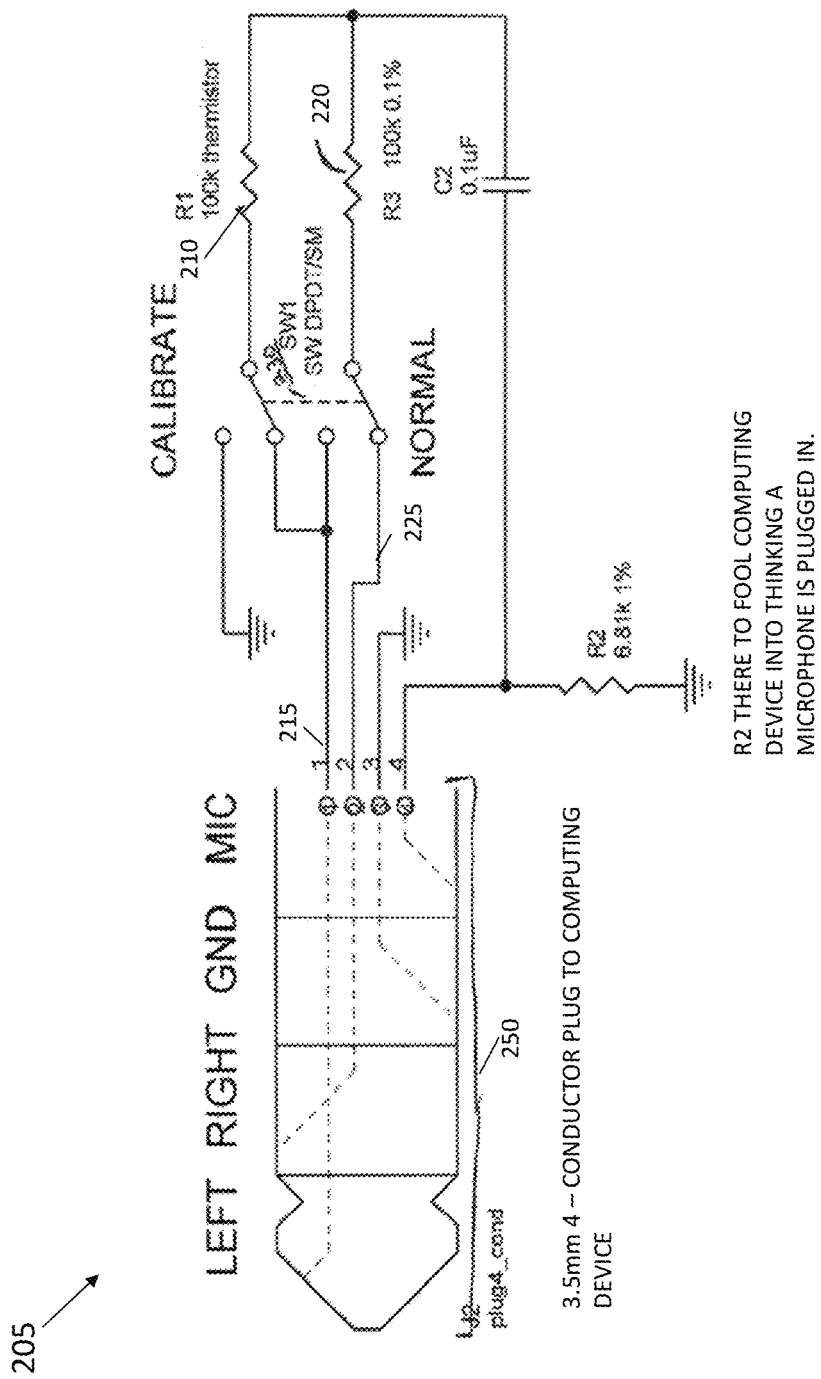
FIG. 2 is a schematic diagram showing a detailed internal view of a temperature sensing probe in accordance with at least one embodiment disclosed herein.

Turning now to FIG. 2, a schematic diagram is provided showing an internal view of temperature sensing probe 205 in accordance with one or more implementations. As referenced above, in certain implementations, temperature sensing probe 205 includes a projecting connector/plug 250, such as a TRS or TRRS connector, as are known to those of ordinary skill in the art. Temperature sensing probe 205 may also include a thermistor 210 and a resistor 220. Thermistor 210 is operatively connected to a conductor 215 that extends to a particular area or region of connector 250. It should be understood that thermistor 210 changes resistance according to temperature, as is known to those of ordinary skill in the art. Thermistor 210 can be a standard type thermistor used in digital oral thermometers, such as those that have a +/−0.1 C tolerance. Resistor 220 is operatively connected to another conductor 225 that extends to another area or region of connector 250. FIG. 2 depicts an exemplary configuration of the areas of connector 250 and the various connectors that are associated with each area. For example, it can be appreciated that conductor 215 extends to the 'LEFT' area of connector 250 (corresponding to the left stereo headphone channel) while conductor 225 extends to the 'RIGHT area of connector 250 (corresponding to the right stereo headphone channel). As will be described in greater detail herein, by transmitting and receiving signals through the various conductors 215, 225, computing device 105 can compute a temperature sensed at probe 205.

In certain implementations, temperature sensing probe 205 also includes a calibrator, which may include a switch 230. Calibration may be used in one or more implementations to identify a suitable linear range for accurate temperature readings. For example, if volume output is too low, noise will cause inaccurate measurement. Similarly, if the microphone gain is too high, the signal will saturate and will similarly cause inaccurate measurement. Moreover, as noted herein, discrepancies between output channels (L/R) may need to be identified for proper calibration. In accordance with one or more implementations of the present application, calibration is provided for the linear range of determining temperature with ranges associated with the human body.

Upon activation of the switch 230, the conductor 215 can be disconnected from thermistor 210, and connected to resistor 220. Additionally, in certain implementations, activation of the switch 230 serves to ground thermistor 210, in a manner known to those of ordinary skill in the art. Further, headphone output signals that come from the computing device 105 go through C2 and back to computing device 105 via microphone input 250, thereby enabling computing device 105 to make measurements.

The operation of the temperature measuring system 100 and the various elements and components described above will be further appreciated with reference to the methods described below, in conjunction with FIGS. 3-4.

Figure 3:
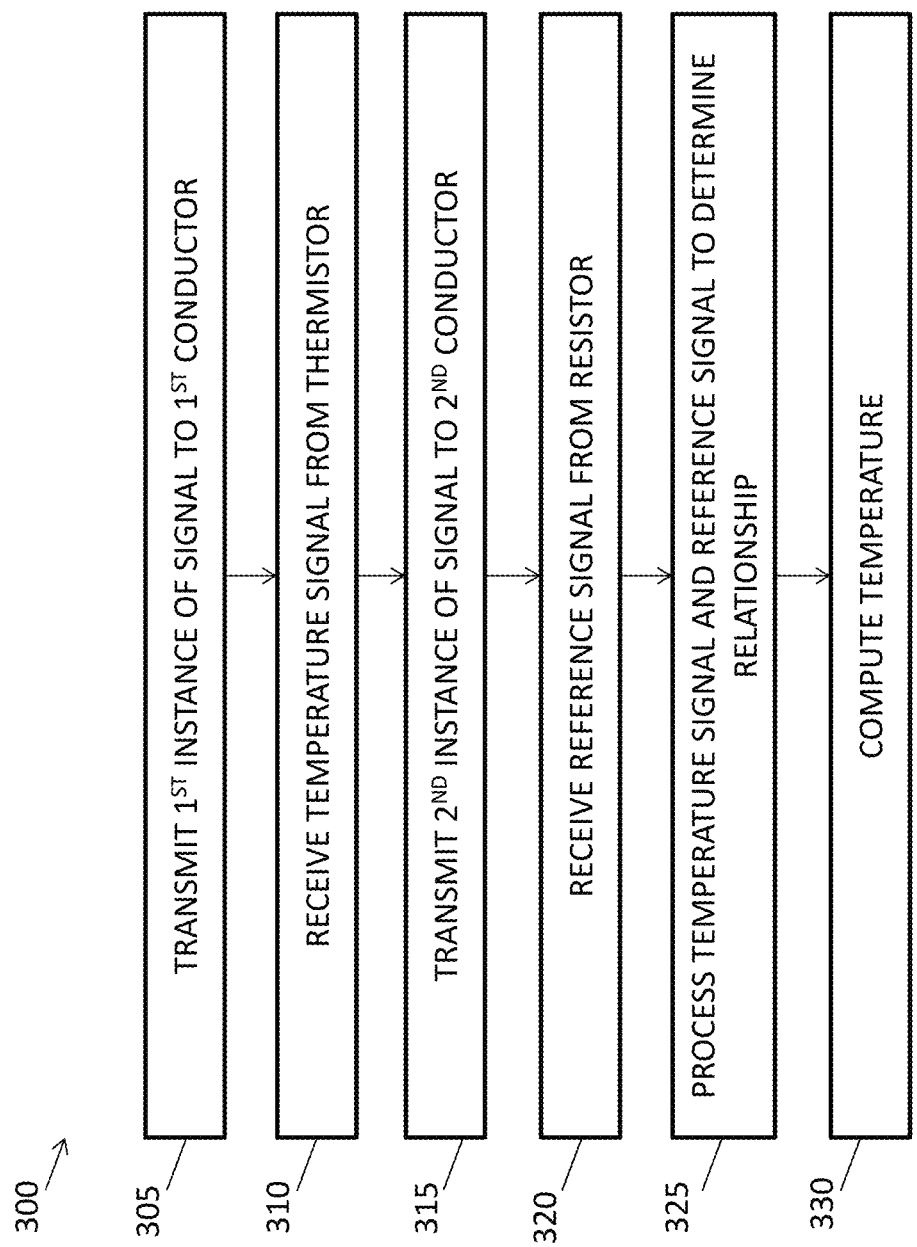
FIG. 3 is a flow diagram showing a routine that illustrates a broad aspect of a method for measuring temperature in accordance with at least one embodiment disclosed herein.

Turning now to FIG. 3, a flow diagram is described showing a routine 300 that illustrates a broad aspect of a method for measuring temperature in accordance with at least one embodiment disclosed herein. It should be appreciated that several of the logical operations described herein are implemented (1) as a sequence of computer implemented acts or program modules running on computing device 105 and/or (2) as interconnected machine logic circuits or circuit modules within computing device 105. The implementation is a matter of choice dependent on the requirements of the device (e.g., size, energy, consumption, performance, etc.). Accordingly, the logical operations described herein are referred to variously as operations, steps, structural devices, acts, or modules. As referenced above, various of these operations, steps, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

The process begins at step 305 and processor 110 executes one or more of software modules 130, including, for example, temperature determination application 170, configures computing device 105 to transmit a first instance of a signal to conductor 215. It should be understood that in certain implementations, the referenced signal (and various other signals referenced herein) may be an audio tone (such as a 1 kHz tone). It should be further understood that the signal may be output through a specific output of headphone jack 155, such as the left headphone output, as is known to those of ordinary skill in the art. In doing so, the tone can be received by conductor 215 at connector 250 (which also corresponds to the left headphone, and is thus aligned with the appropriate output region of headphone jack 155 when inserted therein).

Then, at step 310, processor 110 executing one or more of software modules 130, including, for example, temperature determination application 170, configures computing device 105 to receive a temperature signal from the thermistor 210. The temperature signal may correspond to the first instance of the signal (that is, the signal transmitted at step 305) as output or returned from the thermistor 210. In doing so, the amplitude of the signal being returned from thermistor 210 can be measured, as is known to those of ordinary skill in the art. The signal received at step 310 and the signal received at step 320 can be compared in order to determine the resistance of thermistor 210, in a manner known to those of ordinary skill in the art. Accordingly, it can be appreciated that the larger the resistance of thermistor 210, the smaller the signal received at step 310 can be based on a simple resistive divider circuit, as is known to those of ordinary skill in the art.

At step 315, processor 110 executing one or more of software modules 130, including, for example, temperature determination application 170, optionally configures computing device 105 to transmit a second instance of the signal to conductor 225.

Then, at step 320, processor 110 executing one or more of software modules 130, including, for example, temperature determination application 170 configures computing device 105 to receive a reference signal from the resistor 220. The reference signal corresponds to the second instance of the signal (that is, the signal transmitted at step 305) as output from the resistor 220.

At step 325, processor 110 executing one or more of software modules 130, including, for example, temperature determination application 170 configures computing device 105 to process the temperature signal and the reference signal to determine a relationship between the temperature signal (received at step 310) and the reference signal (received at step 320). It can be appreciated that use of this ratiometric method cancels out any effects and tolerances of other conductors (e.g., C2 and R2 in FIG. 2), as well as the input circuitry of computing device 105.

Then, at step 330, processor 110 executing one or more of software modules 130, including, for example, temperature determination application 170 configures computing device 105 to compute a temperature based on the relationship determined at step 325.

Figure 4:
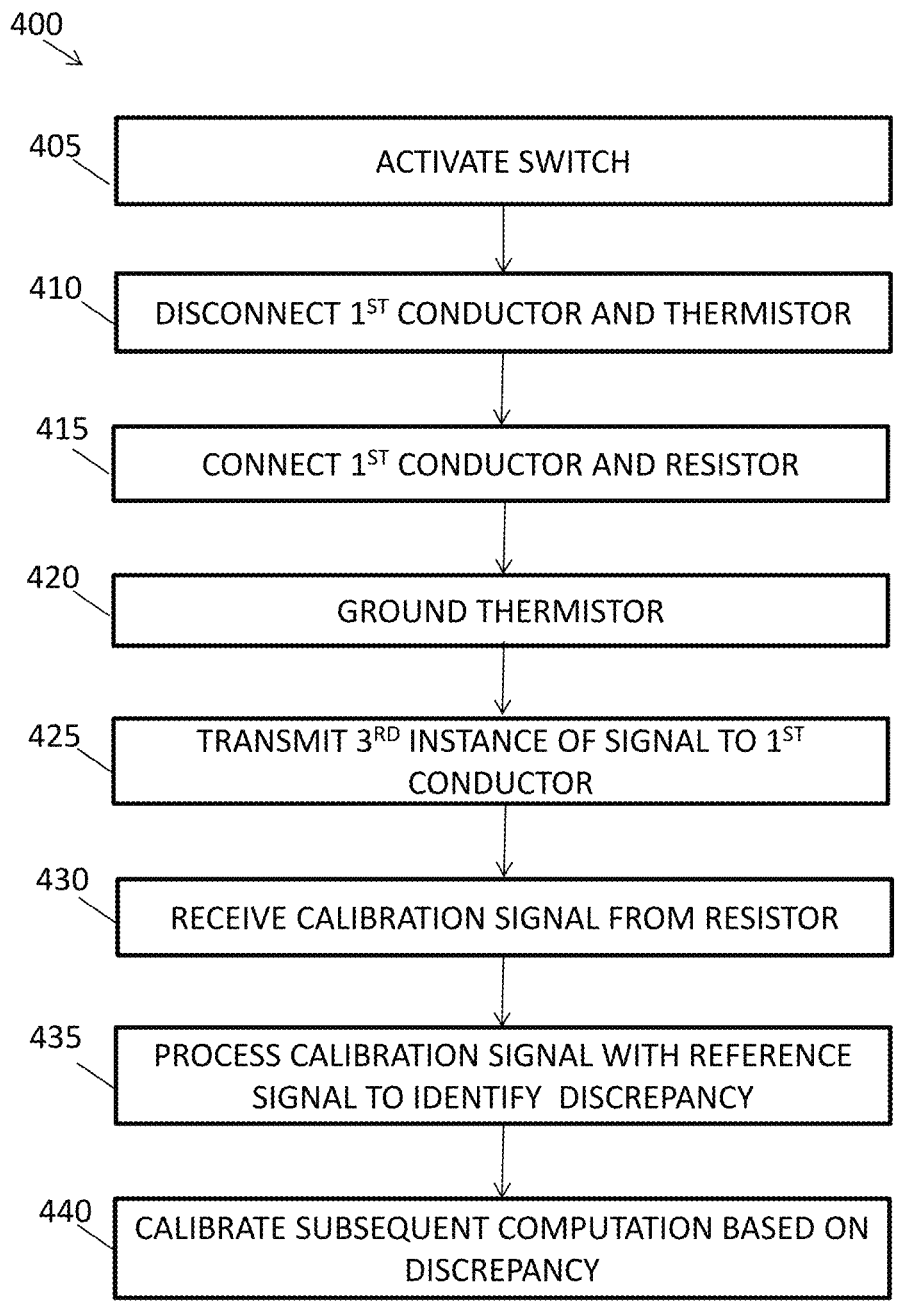
FIG. 4 is a flow diagram showing a routine that illustrates a broad aspect of a method for calibrating a temperature measuring system in accordance with at least one embodiment disclosed herein.

Turning now to FIG. 4 a flow diagram is described showing a routine 400 that illustrates a broad aspect of a method for calibrating a temperature measurement system in accordance with at least one embodiment disclosed herein.

The process begins at step 405 where processor 110 executing one or more of software modules 130, including, for example, calibration application 172, configures computing device 105. Switch 230 may be activated, for example, by a user or by the computing device 105. Upon activation of switch 230, conductor 215 is disconnected from thermistor 210 (step 410) and connected to resistor 220 (step 415), as referenced above. Activation of switch 230 can also ground thermistor 210 (step 420).

Then, at step 425, processor 110 executing one or more of software modules 130, including, for example, calibration application 172, configures computing device 105 to transmit a third instance of the signal to conductor 215.

At step 430, processor 110 executing one or more of software modules 130, including, for example, calibration application 172, configures computing device 105 to receive a calibration signal from resistor 220. The calibration signal corresponds to the third instance of the signal as output/returned from the resistor 220.

Then, at step 435, processor 110 executing one or more of software modules 130, including, for example, calibration application 172, configures computing device 105 to process the calibration signal (received at step 430) with the reference signal (received at step 320) in order to determine whether there any discrepancies between the two respective (headphone) output signals. In doing so, one or more discrepancies between the calibration signal and the reference signal can be identified. In an alternative implementation, other parameters may be considered, such as to determine a suitable headphone output volume to use for optimal signal levels, quiescent noise level, or the like. In this way, a suitable headphone output volume, optimal microphone input gain or the like is provided for an adequate signal-to-noise ratio, and/or to utilize the linear portion of the microphone input.

It can be appreciated that the referenced calibration method can be necessary in light of the fact that there is no way to ensure that the left and right headphone outputs of computing device 105 are exactly the same. As such, switch 230 can switch between the normal and calibration mode. In the calibration mode, the left headphone output (corresponding to conductor 215) is connected to resistor 220, and thermistor 210 is connected to ground. This in effect simulates swapping the left and right headphone output connections, allowing computing device 105 to determine exactly what the differences are between the left and right headphone outputs. It should be noted that in calibration mode, thermistor 210 is connected to ground (instead of to the right headphone output) in order to enable computing device 105 to definitively determine when the calibration mode has been activated (there will be no input when the computing device drives the right headphone signal).

At step 440, processor 110 executing one or more of software modules 130, including, for example, calibration application 172, configures computing device 105 to calibrate a subsequent computation based on the discrepancy identified at step 435.

Figure 5:
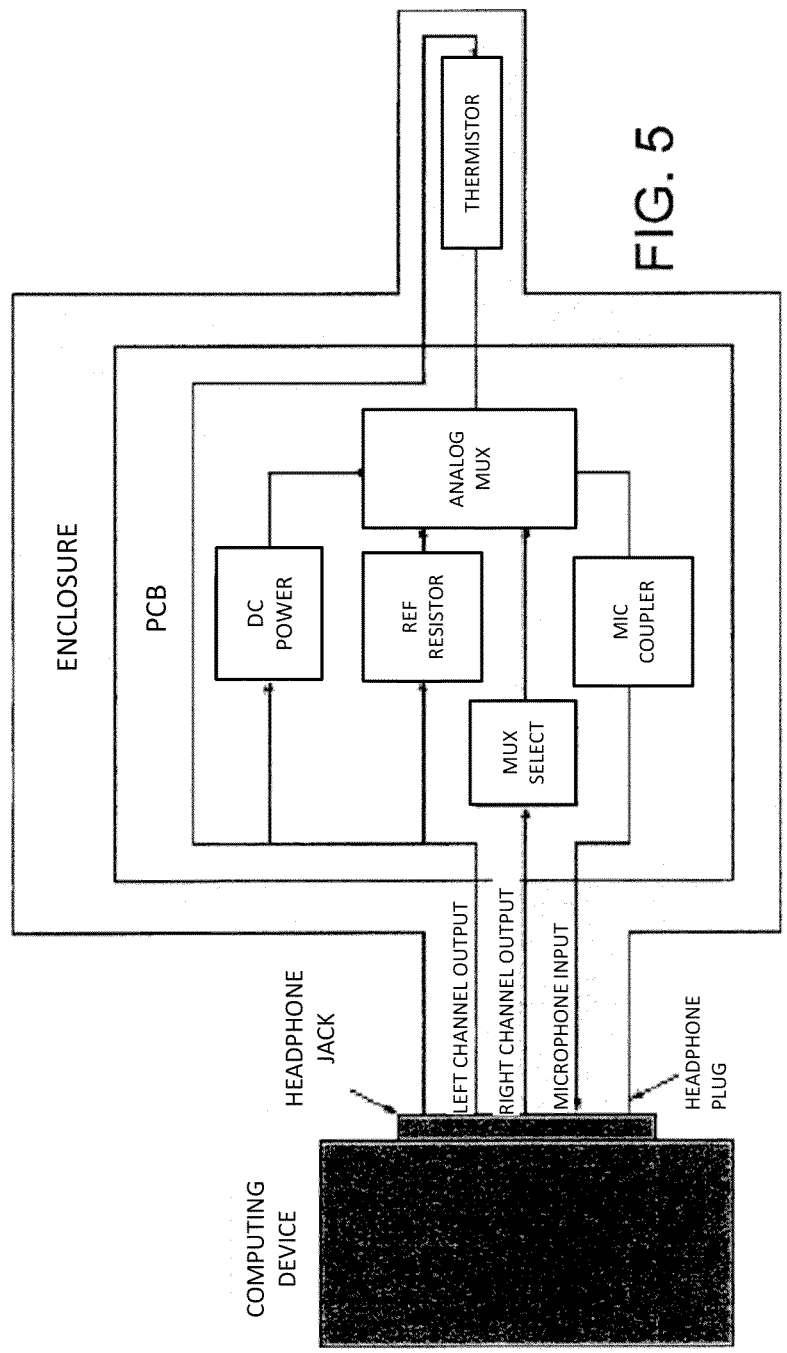
FIGS. 5-6 depict further aspects of the systems and methods described herein.
Figure 6:
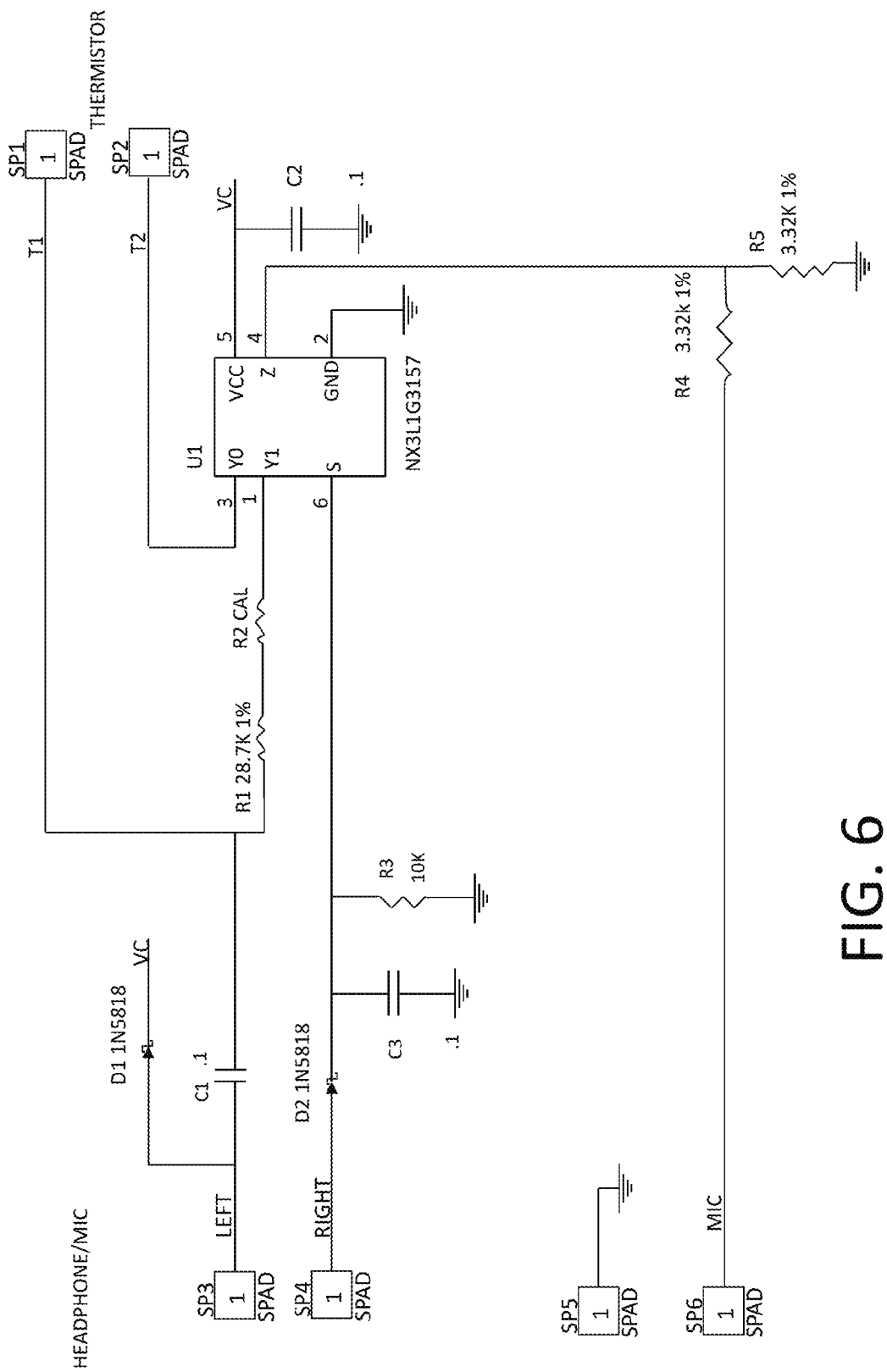

FIG. 5 depicts another implementation of temperature sensing probe 205, including an enclosure, headphone plug, thermistor, temperature sensing probe PCB—Sections (e.g., as shown in FIG. 6), DC Power (the DC Power section (D1, C2) generates approximately 1.6 volts from the audio tone on the left channel output for the operation of the Analog Mux), Resistor (the Reference Resistor section (R1, R2) matches the value of the thermistor at 37 C), Mux. Select (the Mux. select section (D2, C3, R3) generates the mux select from the audio tone on the right channel output), Analog Mux (the Analog Mux. section (U1) connects the thermistor or the Reference Resistor from the left channel output to the Mic. Coupler), and/or Mic. Coupler (the Mic. Coupler section (R4,R5) presents the proper resistance (6.8K) to the computing device's microphone input. The microphone coupler section also attenuates the left channel output by the correct amount and connects to the computing device's microphone input). In alternative implementations, temperature sensing probe PCB may include a power harnessing circuit (not shown) in lieu of a DC power source (e.g., one or more batteries). The power harnessing circuit may include, for example, a voltage multiplier and a rectifier.

Moreover, in certain implementations (such as with reference to the implementation illustrated in FIG. 2), the methods described herein can be configured as follows:

If the computing device detects the correct resistance on the microphone input it outputs a tone on the left channel output and delays TBD ms.

The computing device measures the amplitude on the microphone input and saves it as the thermistor measurement value.

The computing device outputs a tone on the right channel output and delays TBD ms.

The computing device measures the amplitude on the microphone input and saves it as the Reference Resistance measurement value.

The computing device calculates the thermistor resistance using the ratio of the thermistor measurement value and the Reference Resistance measurement value.

The computing device calculates the thermistor temperature by using the calculated thermistor resistance and a thermistor RT table or thermistor RT equation.

As described herein a computing device connected thermometer provides a simple, extremely low-cost device-enabled thermometer that provides actionable information, as opposed to just a number count, and tracks health and obtain advice from one or more medical professionals using an associated mobile application. The mobile software application includes a user-friendly interface that allows users to contact a medical professional, compare symptoms to "what's going around" in the local area, and keep records of health issues. It also provides several additional services and features that enable users to schedule appointment and contact urgent care facilities.

In an implementation, the main menu of the software application includes primary sections: Health and Groups and Places. With regard to Health, options are provided for Obtain a Reading; Family Profiles and Find Care. In an embodiment, when a user taps the 'take a reading' button, a numerical readout is displayed on the user's display screen, after which the user is redirected to the symptoms screen to add symptoms to the current reading. Upon tapping the 'Find Care' button, users are redirected to a screen that presents with options, including booking an appointment at a local urgent care facility, calling a nurse directly and immediately (upon which the software application connects the user to a nurse call center) and other features.

In connection with groups and places, "social" feature are provided that inform the user of symptoms, illnesses and related trends that are going around in the local area or in a group at the current time—essentially the health weather. Other features and functionalities provided by the software application include, for example, temperature tutorial/instructions. In this case, users of the thermometer/app interact with a temperature tutorial to get acquainted with the software application, and its different features and functionalities. Users may also be prompted on how to use the thermometer during temperature taking. In healthcare terms, this is similar to an IFU (instructions for use) insert for a medical product. The present application, however, integrates instructions during product use, which provides a unique system and method for prompting users how to use a product while the user simultaneously uses the software application—and as a replacement or supplement for an IFU for FDA purposes.

In addition, the computing device provides notifications, which may, depending upon one or more platforms and operating systems (e.g., iOS, ANDROID AND WINDOWS Phone) code of the project may be divided into several layers, including: data layer (platform independent layer); platform manager layer. (platform dependent layer); and presentation layer. The data layer may be responsible for: generation audio output stream, processing audio input stream, calculation resistance of thermistor, calculating temperature, prediction stabilization temperature. The platform manager layer may be responsible for platform dependent configuration of audio output and audio input, audio exchange, for handling events of connection/disconnection thermometer to/from the computing device, saving/loading calibration settings. Moreover, the presentation layer may be responsible for: providing a user interface, saving user data, and communicating with web services.

Figure 7:
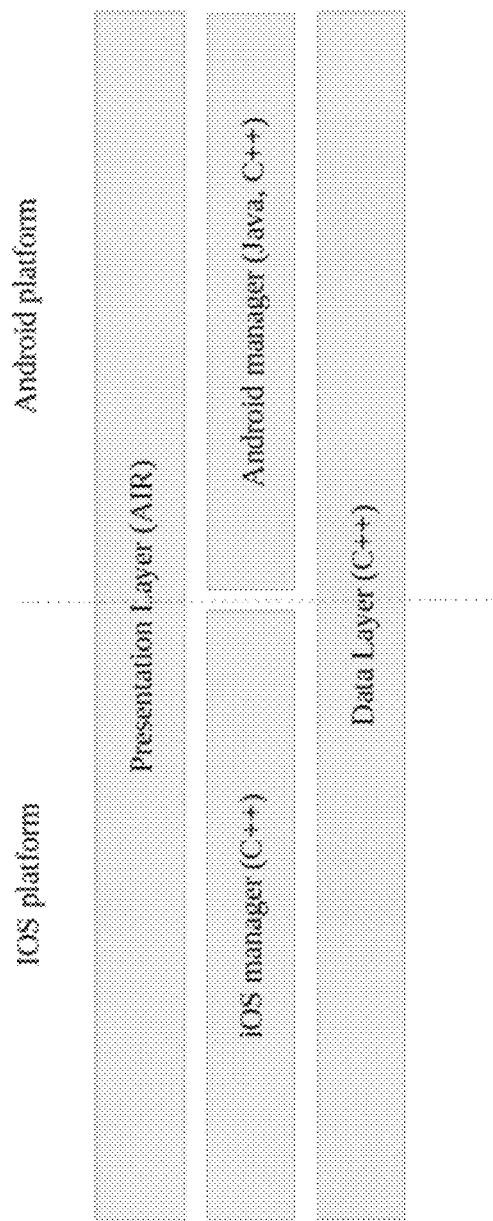
FIG. 7 illustrates an example implementation in accordance with the iOS and Android platforms.

An implementation in accordance with the iOS and Android platforms is shown in FIG. 7.

Figure 8:
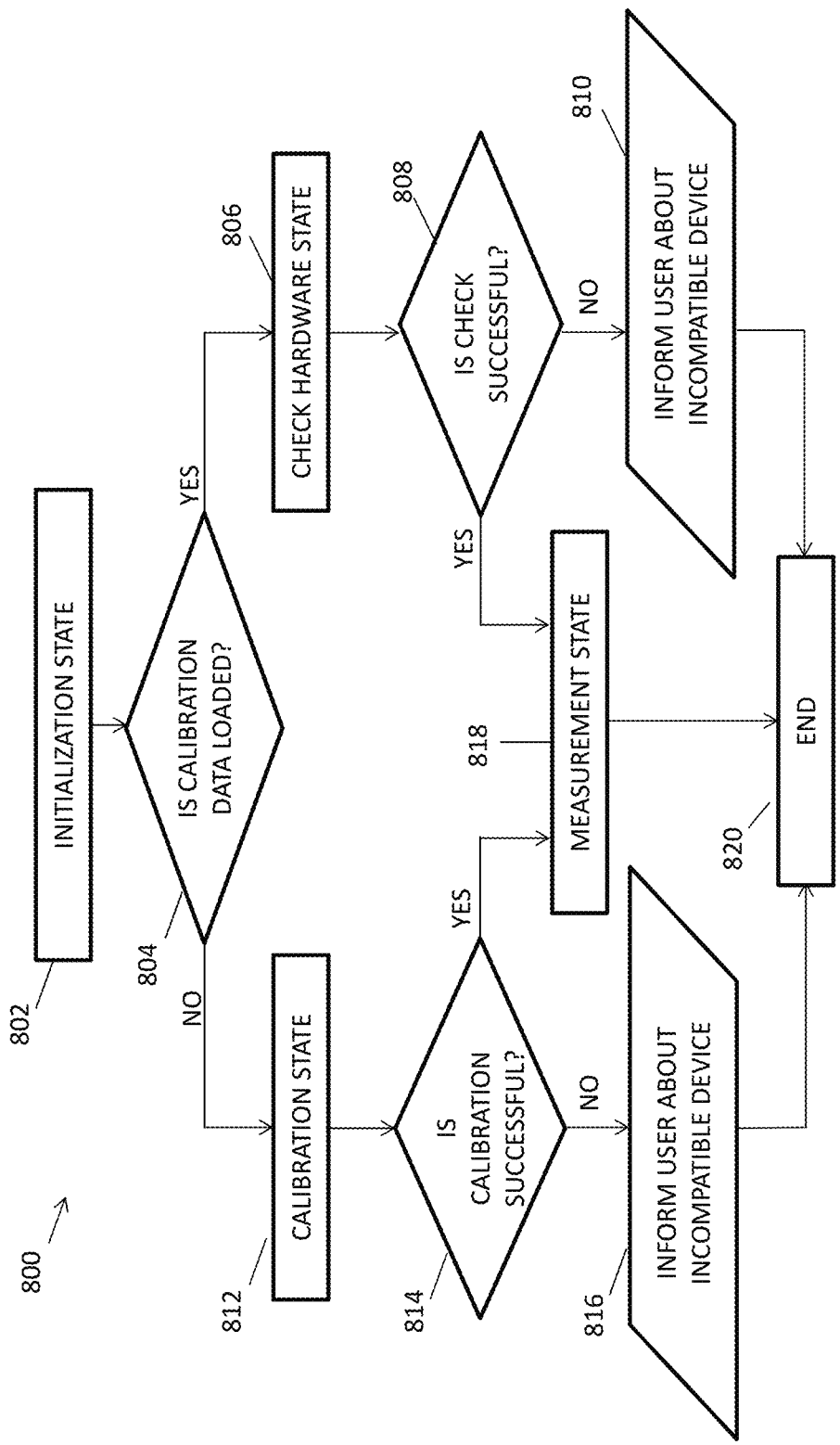
FIG. 8 is a flowchart showing example steps associated with a workflow in connection with an implementation of the present application.

FIG. 8 is a flowchart showing example steps 800 associated with a workflow in connection with an implementation of the present application. As shown in FIG. 8, during the initialization state (802), the computing device starts and tries to load calibration settings (noise level, gain value, left to right channel ratio) (804). If calibration settings loading was successful, the process continues to check hardware state (806), and a determination is made whether the check hardware state is successful (808). If the hardware check failed, then a prompt is displayed for the user to check the connection (810). If calibration settings loading failed in step 804, the process branches to the calibration state (812), and a determination is made whether the calibration was successful (814). If the hardware check failed, then a prompt is displayed for the user that the device may be incompatible (816). If the determination at steps 808 and 814 that the hardware check and calibration were successful, the computing device performs measuring of signal with different gain values to detect optimal gain value for device (818). Thereafter, the process ends (820).

A description of operation steps associated with one or more implementations of the present application is now provided. A signal is transmitted which crosses the thermistor and information is read back. The computing device generates tones on left channel, and performs measurement of input signal amplitude ($A_{therm}$). Moreover, a signal is passed through thermistor. The computing device generates tones on right channel, and performs measurement of input signal amplitude ($A_{ref}$). Signal is passed through a resistor (referred to herein, generally, as a reference resistor. The computing device calculates the thermistor's resistance using calibration data (left to right channel ratio—LTRRatio) and the reference resistor resistance value ($R_{ref}$). $R_{therm}=R_{ref}*LTRRatio*A_{ref}/A_{therm}$. The computing device converts thermistor's resistance to temperature using provided by respective thermistor's manufacturer conversion data, then stores time and temperature value. Using stored values of time and temperature, the computing device predicts stabilization temperature of thermistor.

A description of steps associated with determining optimal gain value for device during calibration (one of the calibration steps), is now provided.

The computing device performs measuring of signal with different gain values to detect optimal gain value for device. This may relate, for example, to different headphone output volume and microphone input gain values. As used herein, optimal gain refers to a middle point of range where input amplitude is linear. If input amplitude is not linear enough, or optimal gain is lower than 10%, then the process provides a message to the display screen that the device is not compatible.

Figure 9:
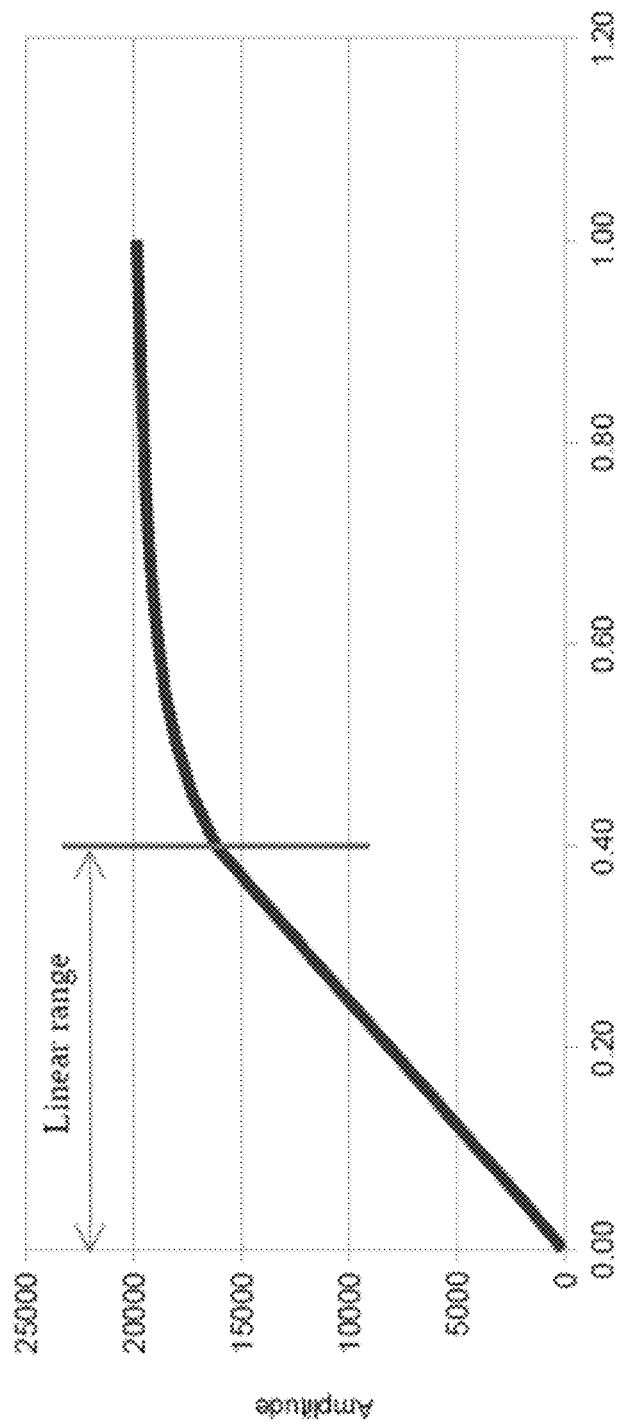
FIG. 9 illustrates graph of input signal amplitude versus gain value.

FIG. 9 illustrates a graph of input signal amplitude versus gain value. Accuracy measurement is significantly improved as a function of the linear range of the graph.

Figure 10:
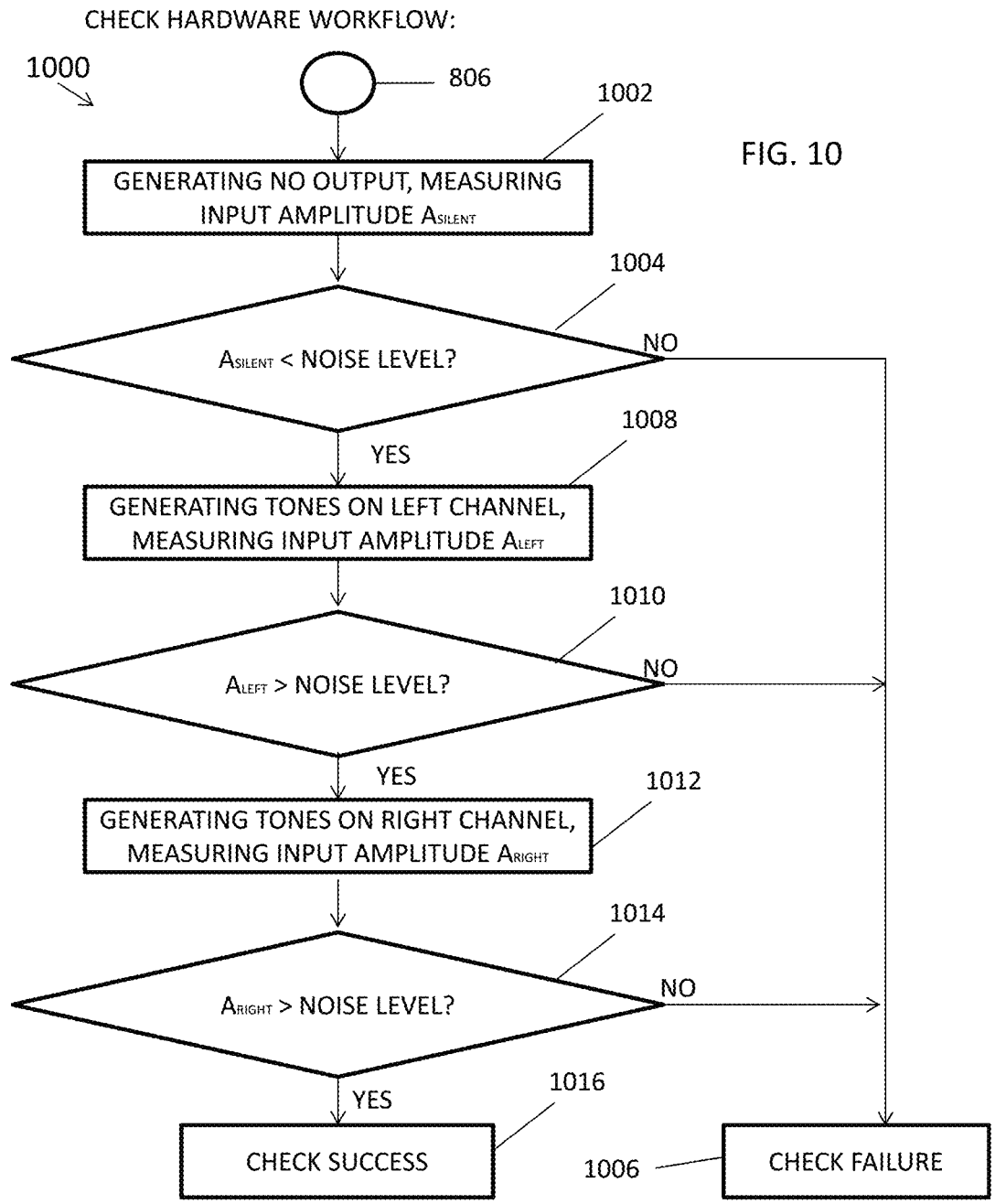
FIGS. 10-12 are additional flowcharts showing example steps associated with the check hardware workflow, the calibration workflow and the measuring workflow.

FIG. 10 is a flowchart showing example steps 1000 associated with check hardware state (806, FIG. 8). At step 1002, the computing device may perform an input signal amplitude measurement without generating any output tones. Thereafter, a determination is made whether the input amplitude of a silent signal is higher than loaded noise level of device (1004). If not, then a message is provided to check the temperature sensing probe 205 (1006). Otherwise, the computing device generates one or more tones on the left channel, and performs signal amplitude measuring (1008). Thereafter, a determination is made whether the signal amplitude is less than loaded noise level (1010). If not, then a message appears to prompt the user to check the temperature sensing probe 205 (1006). Otherwise, the computing device thereafter generates tones on right channel, and performs signal amplitude measuring (1012). Thereafter, a determination is made whether the signal amplitude is less than loaded noise level (1014). If not, a message appears to prompt the user to check the temperature sensing probe 205 (1006). Otherwise, thereafter the process branches to the measuring state (1016).

Figure 11:
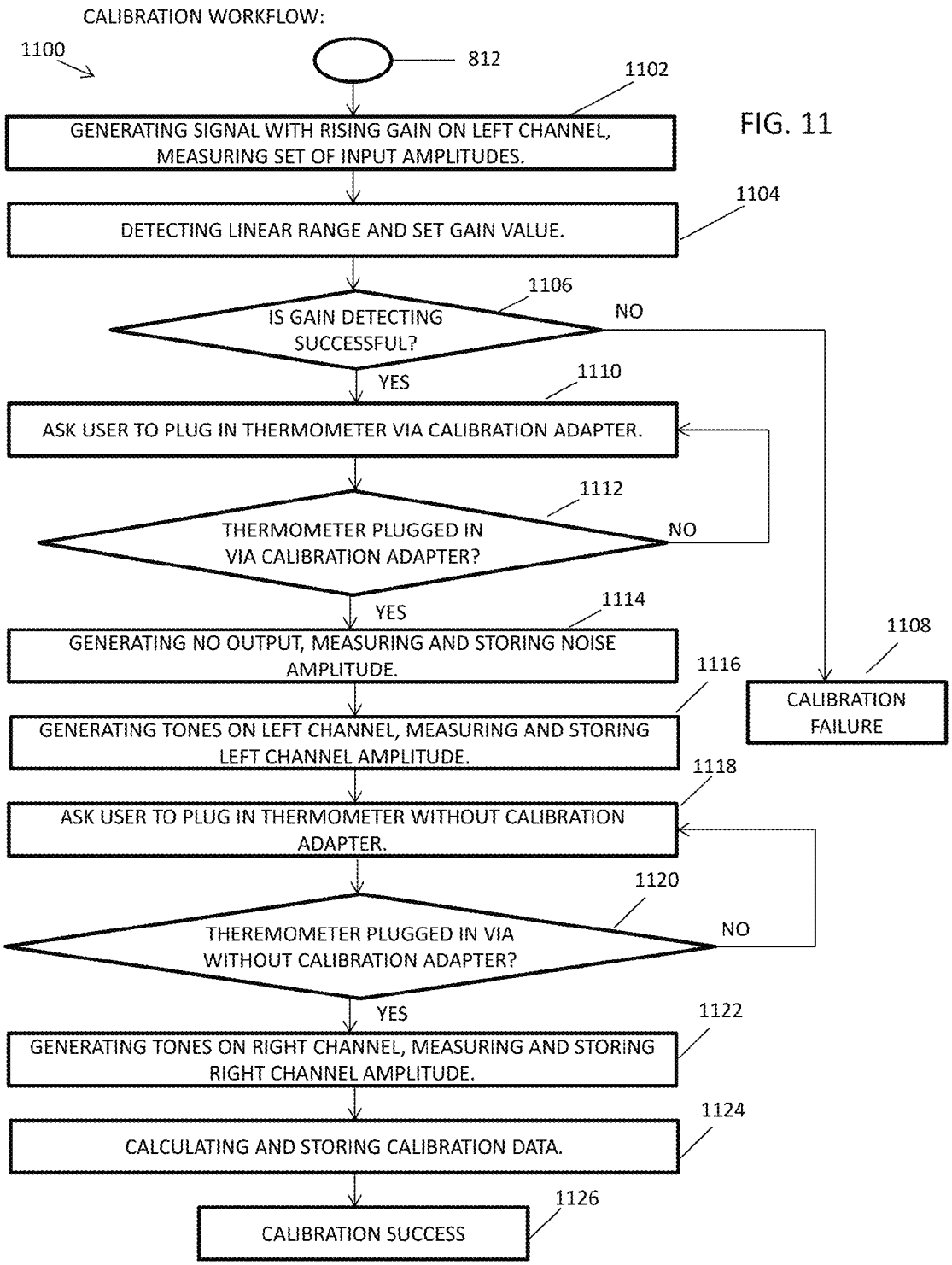

FIG. 11 is a flowchart showing example steps 1100 associated with check calibration (812, FIG. 8). In one or more alternative implementations of the present application, a calibration adapter is provided into which a temperature sensing probe 205 inserts, and which is inserted into computing device 105. With reference to FIG. 11, in such alternative implementation, the computing device generates a signal with a rising gain on the left channel, and measures a set of input amplitudes (1102). Linear ranges are detected and a gain value is set (1104). Thereafter, a determination is made whether gain detecting is successful (1106). If not, the process branches to 1108 and calibration failure is determined. Otherwise, the computing device prompts a user to plug the temperature sensing probe 205 into the calibration adapter (1110), and continues to prompt (112) until the user does so. Thereafter, the computing device performs measuring of input tone amplitude without generating output tones, for example, in order to detect a noise level of the microphone jack associated with the mobile device (1114). Thereafter, the computing device generates one or more tones on the left channel and performs signal amplitude measurement, and then stores the measured value (1116). In this case, signal from phone's left channel had passed through reference resistor. Thereafter, the computing device prompts the user to plug in the temperature sensing probe 205 without the calibration adapter (1118) and continues to prompt (1120) until the user does so. Thereafter, the application generates one or more output tones on the right channel and performs a signal amplitude measurement, and then stores the measured value (1122). In this case signal from phone's right channel passed through reference resistor. Thereafter, the computing device calculates the left to right ratio, and stores calibration data (1124), and the calibration process is successful (1126).

With regard to steps associated with measuring state, the computing device generates tones on left channel, and performs measurement of input signal amplitude ($A_{therm}$). The signal is passed through thermistor. The computing device generates tones on the right channel, and performs measurement of input signal amplitude ($A_{ref}$). The signal is passed through reference resistor. The computing device calculates thermistor's resistance using calibration data (left to right channel ratio—LTRRatio) and reference resistor resistance value ($R_{ref}$).

$$R_{therm}=R_{ref}*LTRRatio*A_{ref}/A_{therm}.$$

Thereafter, the computing device converts the thermistor's resistance to temperature using information provided by the respective thermistor's manufacturer conversion data, and then stores time and temperature value. Using stored values of time and temperature, the computing device predicts stabilization temperature of thermistor.

Figure 12:
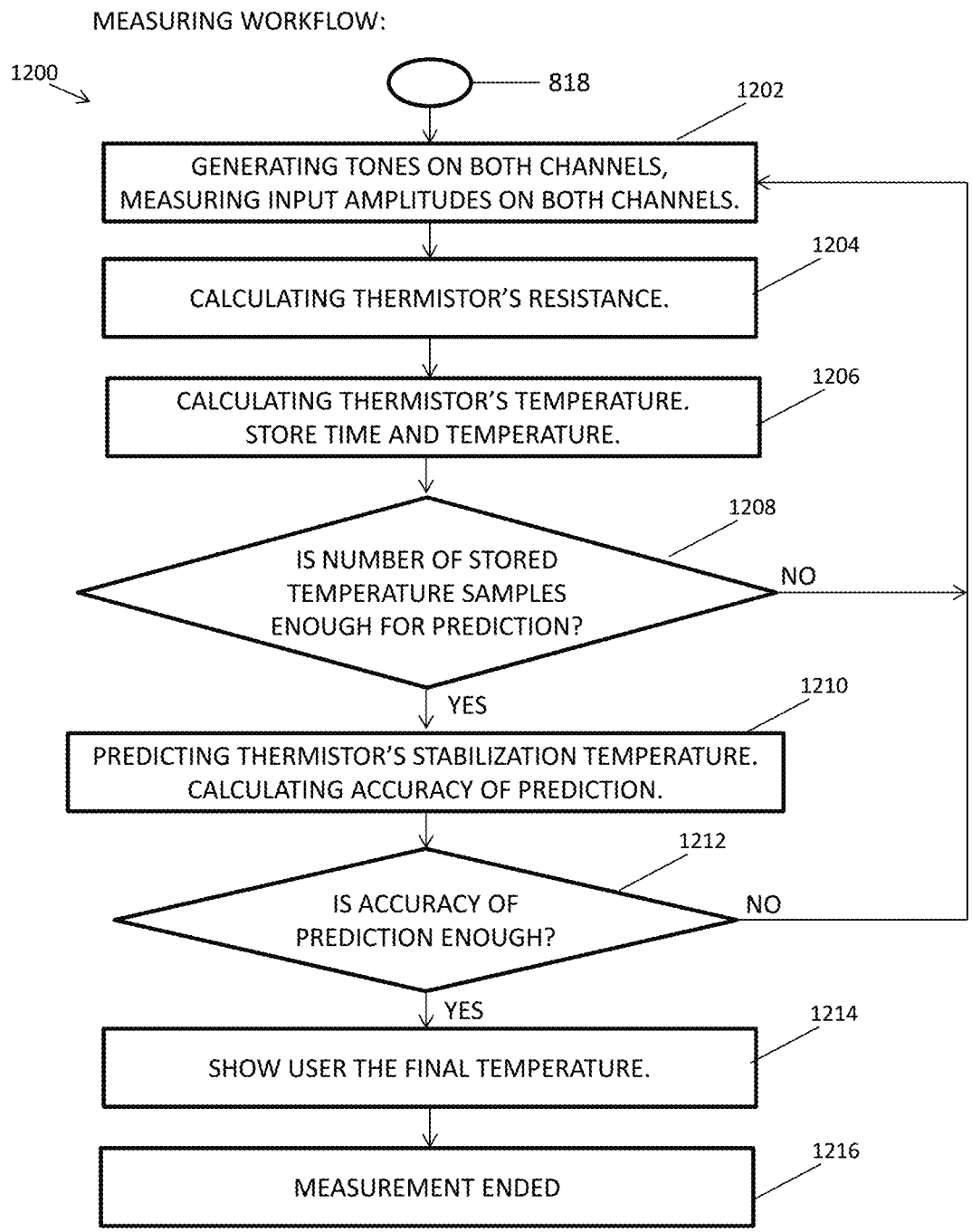

FIG. 12 is a flowchart showing example steps 1200 associated with measuring workflow (818, FIG. 8). At 1202, tones are generated on both channels, and input amplitudes are measured on both channels. Thereafter, the thermistor's resistance is calculated (1204). The thermistor's temperature, thereafter, is calculated and the time and temperature are stored (1206). Thereafter a determination is made whether the number of stored temperature samples is sufficient for an accurate prediction (1208). If not, then the process branches back to step 1202. Otherwise, the process continues to 1210, and the computing device predicts the thermistor's stabilization temperature and calculates the accuracy of the prediction. A determination is made, thereafter, whether the prediction is sufficiently accurate (1212). If not, then the process branches back to step 1202. Otherwise, the temperature is displayed (1214) and the process ends (1216).

A discussion is now provided in connection with input stream processing. In case the mobile device has two output channels and one input channel, the data layer may have to recognize which tone comes from the left channel, and which tone comes from the right channel. This may be, for example, due to a temporal latency between the time when the computing device 105 sends a tone and the device's 105 buffer(s) are full of received information via the microphone input. The present application determines this by placing <<frequency markers>> into output stream.

FIG. 13 illustrates an example output stereo stream and a corresponding input monaural ("mono") stream. The present application analyzes input tones and calculates the tones' frequencies. In an embodiment, a data layer algorithm separates tones that come from the left channel and tones that come from the right channel: tones after <<Frequency marker 1>> are left channel tones (tones passed through thermistor), tones after <<Frequency marker 2>> are right channel tones (tones passed through reference resistor).

The present application is now further described with reference to example circuit diagrams of implementations shown in FIGS. 14-16.

Figure 14:
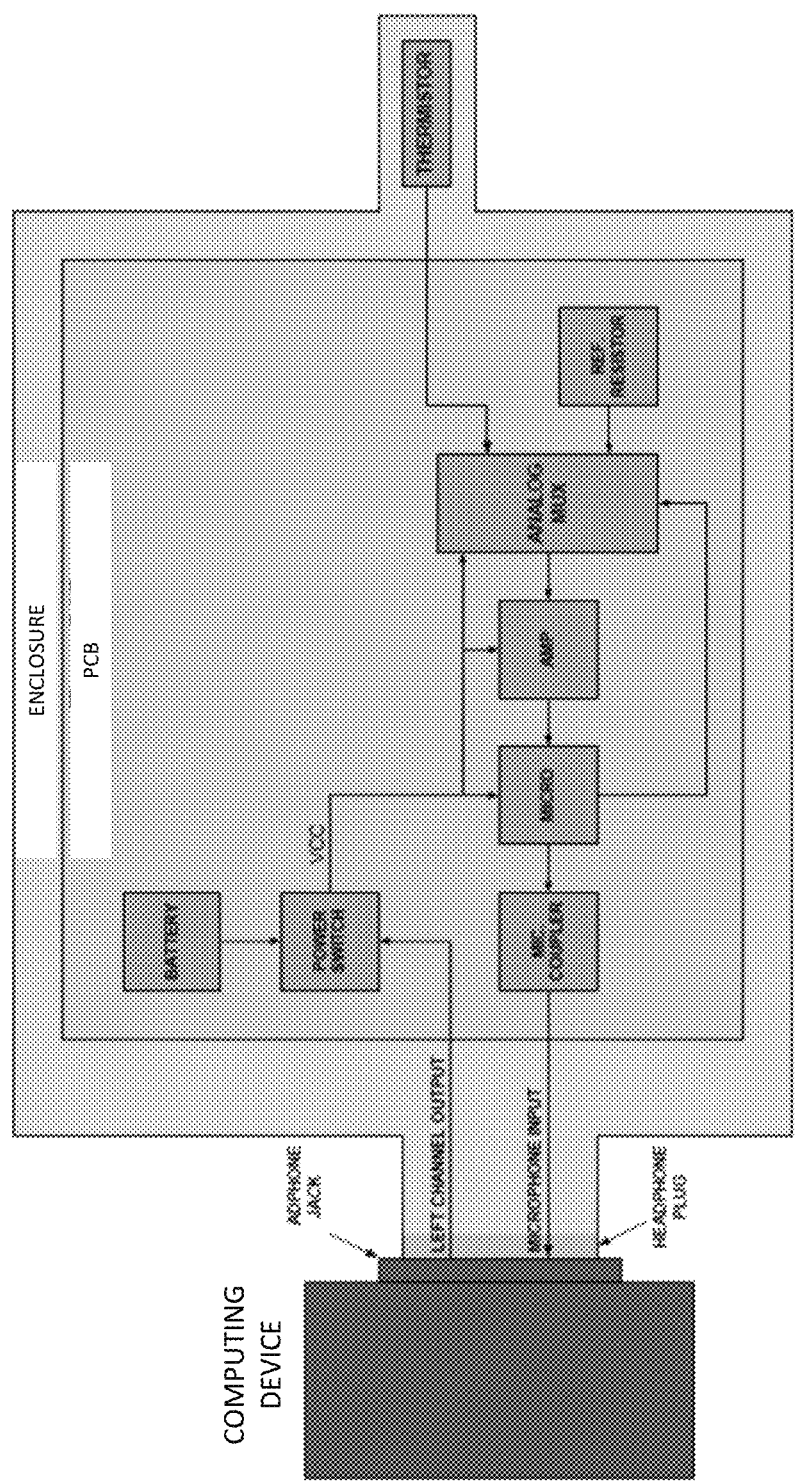
FIG. 14 is a circuit diagram illustrating an implementation of the present that includes a thermometer that includes a microprocessor.

FIG. 14 is a circuit diagram illustrating an example implementation of computing device connected temperature probe that includes a processor and corresponding firmware. This approach results in a product that may be self-powered, and that overcomes a need to power the device from a computing device's headphone jack. The design illustrated in FIG. 14 further addresses challenges associated with variability of voltage and current output across devices of various types and even within a specific type. For example, variations from HTC devices, to iPhone 5 of 0.77 vpp to greater than 3 vpp are addressed.

One particular benefit of the design illustrated in FIG. 14 is to overcome challenges associated with variability of microphone gain. The result is an ultra-low-cost device-connected thermometer product that communicates with a computing device using tones to receive the temperature value from the microprocessor. As shown in FIG. 14, this design includes an enclosure, headphone plug, thermistor, and temperature sensing probe circuitry sections. The circuitry section include a power source, that may be a battery or power harnessing circuit to supply voltage, a power switch that connects the power source to the other sections, based on an audio tone from the computing device's left channel headphone output. Further, a reference resistor section is provided that matches the value of the thermistor at 37 c. An analog mux is included that connects the thermistor or the reference resistor to the amp section. The mux select is controlled by the microprocessor. The Amp provides gain and offset signal processing to provide an amplified voltage to the microcontroller in order to make more accurate measurements with an analog-to-digital converter inside or otherwise associated with the microcontroller. The microprocessor contains firmware.

The firmware, when executed by the processor, configures the processor to perform the following steps:

The temperature of the thermistor is calculated by reading the voltage from the Amp with an internal (or external) analog-to-digital converter. The processor alternately reads the thermistor and the Reference Resistor voltage to make a relative calculation. The processor sends the temperature value to the computing device, for example, by sending tones via the microphone coupler.

A signal conditioner, which may be a microphone coupler, is provided that converts the output of the processor from a high level digital signal to a low level analog signal for the microphone input of the computing device. The microphone coupler provides the proper resistance to the computing device's microphone input so that the software application operating on the computing device (e.g., smartphone) can detect that the temperature sensing probe is plugged in.

In one or more implementations, temperature measurement in connection with a processor-based design is performed that may include the following steps. If the computing device detects the correct resistance on the microphone input, it outputs a tone on the left channel output which powers up the temperature sensing probe PCB. Using firmware, the processor selects the two voltages (e.g., associated with the reference resistor and the thermistor) via the mux, reads the voltage with an analog-digital converter and records voltage readings. The processor calculates the thermistor temperature based on the voltage readings. The processor sends the temperature value to the computing device, for example, by sending tones via the microphone coupler. Thereafter, the software application operating on the computing device receives the tones sent from the processor and displays the measured temperature. The computing device, thereafter, turns off the left channel output which powers down the temperature sensing probe PCB.

Figure 15:
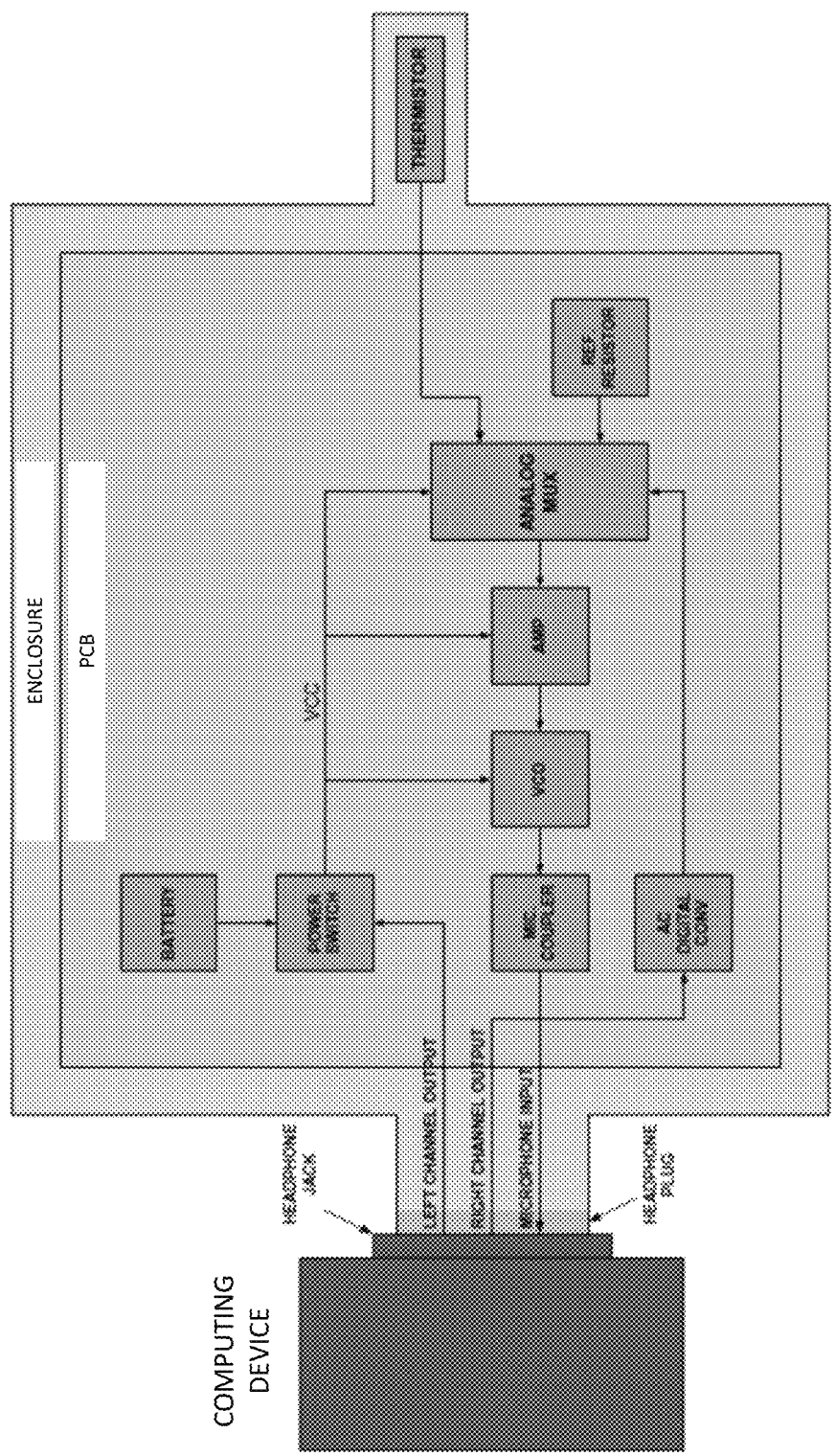
FIG. 15 is a circuit diagram illustrating an implementation of the present application that includes thermometer connected to a computing device and—includes an active circuit (Voltage Controlled Oscillator ("VCO")) non-microprocessor based approach.

FIG. 15 is a circuit diagram illustrating an alternative implementation of an ultra-low-cost computing device connected thermometer includes an active circuit (e.g., a Voltage Controlled Oscillator ("VCO")) non-microprocessor based approach. This design results in a product that is self-powered, which overcomes a need to power the device from a computing device headphone jack and addresses challenges associated with variability of voltage and current output across devices of various types and even within a specific type. For example, variations from HTC devices, to iPhone 5 of 0.77 vpp to greater than 3 vpp are addressed.

In the VCO implementation illustrated in FIG. 15, challenges associated with variability of microphone gain are overcome. The result is an ultra-low-cost computing device connected temperature sensing probe that communicates with the computing device using tones to receive the temperature value from the VCO. In this implementation, custom firmware is not implemented. The temperature calculation and flexibility is provided by the software application operating on the computing device (e.g., the smartphone). As shown in FIG. 15, this design includes an enclosure, a headphone plug, a thermistor, and temperature sensing probe PCB Sections. Those sections include a power source, which may be one or more batteries or may be a power harnessing circuit, to supply voltage. Further a power switch may be provided that connects the power source to the other sections as a function of an audio tone from the computing device. In one implementation, the tone may be transmitted over the left channel headphone output. A reference resistor section is provided that matches the value of the thermistor at 37 C. Moreover, an analog mux is provided that connects the thermistor or the reference resistor voltage to an amplifier. An analog-digital converter is provided that converts the computing device's right channel headphone output into a digital signal to control the mux select which selects the thermistor or reference resistor voltage to the amplifier. The amplifier provides gain and offset signal processing to provide a high level voltage to the VCO. The VCO generates a tone of a frequency that is proportional to the voltage from the amplifier. The VCO tone is transmitted to the microphone coupler. The microphone coupler converts the output of the VCO from a high level digital signal to a low level analog signal that the computing device requires. The microphone coupler provides the proper resistance to the computing device microphone input so that the software application running on the device can detect that the temperature sensing probe is plugged in.

The computing device, when running on the computing device, configures the device to perform the following steps. If the computing device detects the correct resistance on the microphone input, it outputs a tone on the left channel output which powers up the temperature sensing probe PCB. The computing device receives the tone for the reference resistor that is sent from the VCO via the microphone coupler, and measures its frequency and records it. The computing device, thereafter, outputs a tone on the right channel, which selects the thermistor. The computing device receives the tone for the thermistor that is sent from the VCO via the microphone coupler, and measures its frequency and records it. The computing device, thereafter, calculates the thermistor temperature based on the frequency readings, and displays the temperature value. Thereafter, the computing device turns off the left channel output which powers down the temperature sensing probe PCB.

In one or more implementations, a thermometer calibration system and method is provided in accordance with an adapter-based design. FIG. 16, illustrates an example calibration adapter in accordance with one or more implementations of the present application and that comprises an enclosure, headphone plug, and headphone jack and wiring schematic, as well as a components of a temperature sensing probe that include a thermistor, reference resistor, microphone coupler, and headphone plug in accordance with one or more implementations of the present application, temperature sensing probe PCB. The temperature probe PCB includes, for example, a reference resistor that matches the value of the thermistor at 37 C, a microphone coupler section that presents the proper resistance to the computing device microphone input. Moreover, the microphone coupler section also attenuates the left channel output by the correct amount and connects to the computing device microphone input.

In one or more implementations, calibration is performed that may include the following steps. The computing device prompts the user to insert the calibration adapter and the temperature sensing probe into the computing device. If the computing device detects the correct resistance on the microphone input, then a tone is output on the right channel output, measures the amplitude on the microphone input and records the amplitude. If the right channel output amplitude is above a minimum threshold then the computing device prompts the user that the calibration adapter/temperature sensing probe is not detected. If the right channel output amplitude is below a minimum threshold then the computing device outputs a tone on the left channel output, measures the amplitude on the microphone input, and records the amplitude. The computing device prompts the user to remove the calibration adapter and insert the temperature sensing probe into the computing device. If the computing device detects the correct resistance on the microphone input, it outputs a tone on the right channel output, measures the amplitude on the microphone input, and records the amplitude. The computing device calculates the left/right channel ratio and saves it as a calibration value.

In one or more implementations, temperature measurement in connection with an adapter-based design is performed that may include the following steps. If the computing device detects the correct resistance on the microphone input it outputs a tone on the left channel output. The computing device measures the amplitude on the microphone input and saves it as the thermistor measurement value. Thereafter, the computing device outputs a tone on the right channel output. The computing device measures the amplitude on the microphone input and saves it as the reference resistance measurement value. The computing device, thereafter, calculates the thermistor resistance using the calibration value, the ratio of the thermistor measurement value and the reference resistance measurement value. The computing device calculates the thermistor temperature by using the calculated thermistor resistance and a thermistor RT table or thermistor RT equation.

At this juncture, it should be noted that although much of the foregoing description has been directed to systems, methods, and apparatuses for measuring temperature and/or calibrating a temperature measurement system, the systems and methods disclosed herein can be similarly deployed and/or implemented in scenarios, situations, and settings far beyond the referenced scenarios.

It is to be understood that like numerals in the drawings represent like elements through the several figures, and that not all components and/or steps described and illustrated with reference to the figures are required for all embodiments or implementations. It should also be understood that the embodiments, implementations, and/or implementations of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and implementations of the present systems and methods provide a computer implemented method, computer system, and computer program product for measuring temperature and/or calibrating a temperature measurement system. The flowchart and block diagrams in the figures illustrate the architecture, functionality, and operation of possible implementations of systems, methods and computer program products according to various embodiments and implementations. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed:

1. A temperature measuring system comprising:
    a temperature sensing probe having a connector and configured to interface with a computing device via the connector, the temperature sensing probe further comprising a thermistor operatively connected to a first conductor and a resistor operatively connected to a second conductor; and
    a computing device having a first output channel, a second output channel, and a first input channel, the computing device being operatively connected to the temperature sensing probe and further being configured to:
    transmit, over the first output channel, a first instance of a signal to the first conductor;
    receive, over the first input channel, a temperature signal from the thermistor;
    transmit, over the second output channel, a second instance of the signal to the second conductor;
    receive, over the first input channel, a reference signal from the resistor, the reference signal comprising the second instance of the signal as output from the resistor;
    process the temperature signal and the reference signal to determine a relationship between the temperature signal and the reference signal;
    compute a temperature based on the relationship; and
    display temperature information representing the computed temperature.

2. The temperature measuring system of claim 1, wherein the computing device is further configured to:
    provide a prompt for a user to input health information associated with the displayed temperature information;
    receive, in response to the prompt, health information representing at least one of a symptom and an illness; and
    store the received health information in at least one database.

3. The temperature measuring system of claim 1, wherein the computing device is further configured to:
    receive a message; and
    transmit the message to another computing device.

4. The temperature measuring system of claim 1, wherein the computing device is further configured to:
    access at least one database storing health information that represents at least one of a symptom and an illness occurring within a geographic area during a period of time;
    correlate at least some of the health information with the computed temperature; and
    display the correlated at least some of the health information with the temperature information.

5. The temperature measuring system of claim 1, wherein the computing device is further configured to:
    process the temperature to determine a fever; and
    display temperature information representing the temperature and a message that the temperature represents a fever.

6. The temperature measuring system of claim 1, wherein the computing device is further configured to:
    access at least one database storing health information that represents at least one of an illness and a symptom occurring within a geographic area during a period of time; and
    provide a prompt for a user, wherein the prompt is for the user to provide a symptom associated with the computed temperature and/or an illness associated with the computed temperature.

7. The temperature measuring system of claim 6, wherein the computing device is further configured to:
    receive, in response to the prompt, at least one selection of at least some of the health information; and
    store the at least one selection in the at least one database.

8. The temperature measuring system of claim 1, wherein the computing device is further configured to:
    access at least one database that stores provider information representing at least one healthcare provider; and
    display a message associated with the at least some of the provider information.

9. The temperature measuring system of claim 8, wherein the message associated with the at least some of the provider information is formatted as a prompt, and further wherein the computing device is further configured to:

receive, in response to the prompt, a selection of some of the provider information.

10. The temperature measuring system of claim 9, wherein the computing device is further configured to:
transmit to at least one computing device associated with at least one healthcare provider associated with the selection, information associated with at least some of the selection.

11. A computer-implemented method for measuring temperature with a computing device having a first output channel, a second output channel, and a first input channel, the computing device being operatively connected to a temperature sensing probe, the temperature sensing probe configured to interface with the computing device via a connector, the temperature sensing probe further comprising a thermistor operatively connected to a first conductor and a resistor operatively connected to a second conductor, the method comprising:
transmitting, over the first output channel, a first instance of a signal to the first conductor;
receive, over the first input channel, a temperature signal from the thermistor;
transmitting, over the second output channel, a second instance of the signal to the second conductor;
receiving, over the first input channel, a reference signal from the resistor, the reference signal comprising the second instance of the signal as output from the resistor;
processing the temperature signal and the reference signal to determine a relationship between the temperature signal and the reference signal;
computing a temperature based on the relationship; and
displaying temperature information representing the computed temperature.

12. The method of claim 11, further comprising:
providing a prompt for a user to input health information associated with the displayed temperature information;
receiving, in response to the prompt, health information representing at least one of a symptom and an illness; and
storing the received health information in at least one database.

13. The method of claim 11, further comprising;
receiving a message; and
transmitting the message to another computing device.

14. The method system of claim 11, further comprising:
accessing at least one database storing health information that represents at least one of an illness and a symptom occurring within a geographic area during a period of time; and
providing a prompt for a user, wherein the prompt is for the user to provide a symptom associated with the computed temperature and/or an illness associated with the computed temperature.

15. The method of claim 14, further comprising:
receiving, in response to the prompt, at least one selection of at least some of the health information; and
storing the at least one selection in the at least one database.

* * * * *